United States Patent
Rezaei et al.

(10) Patent No.: US 11,715,200 B2
(45) Date of Patent: Aug. 1, 2023

(54) MACHINE LEARNING-BASED ROOT CAUSE ANALYSIS OF PROCESS CYCLE IMAGES

(71) Applicant: Illumina, Inc., San Diego, CA (US)

(72) Inventors: Naghmeh Rezaei, Redwood City, CA (US); Pedro Miguel Filipe Cruz, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 231 days.

(21) Appl. No.: 17/161,595

(22) Filed: Jan. 28, 2021

(65) Prior Publication Data
US 2021/0241048 A1    Aug. 5, 2021

Related U.S. Application Data

(60) Provisional application No. 62/968,950, filed on Jan. 31, 2020.

(51) Int. Cl.
*G06T 7/00* (2017.01)
*G06T 5/20* (2006.01)
(Continued)

(52) U.S. Cl.
CPC ........ *G06T 7/0012* (2013.01); *G06F 18/2148* (2023.01); *G06F 18/2163* (2023.01); *G06F 18/2433* (2023.01); *G06F 18/24323* (2023.01); *G06N 5/01* (2023.01); *G06N 5/04* (2013.01); *G06N 20/20* (2019.01); *G06T 5/20* (2013.01); *G06V 10/56* (2022.01); *G06V 10/764* (2022.01); *G06V 10/774* (2022.01); *G06V 10/7715* (2022.01); *G06V 10/993* (2022.01);
(Continued)

(58) Field of Classification Search
None
See application file for complete search history.

(56) References Cited

U.S. PATENT DOCUMENTS

2019/0164270 A1* 5/2019 Wardell ................ G06N 20/00
2021/0383538 A1* 12/2021 Deasy ...................... G06T 7/11
(Continued)

FOREIGN PATENT DOCUMENTS

EP          3054279 A1    8/2016
WO       2017106918 A1    6/2017
(Continued)

OTHER PUBLICATIONS

U.S. Appl. No. 17/588,077, filed Jan. 28, 2022, US-2022-0245801-A1, Aug. 4, 2022, Pending.
(Continued)

*Primary Examiner* — Emily C Terrell
*Assistant Examiner* — Nathan J Bloom
(74) *Attorney, Agent, or Firm* — Flaster Greenberg P.C.

(57) ABSTRACT

The technology disclosed relates to classification of process cycle images to predict success or failure of process cycles. The technology disclosed includes capturing and processing images of sections arranged on an image generating chip in genotyping process. Image description features of production cycle images are created and given as input to classifiers. A trained classifier separates successful production images from unsuccessful or failed production images. The failed production images are further classified by a trained root cause classifier into various categories of failure.

17 Claims, 25 Drawing Sheets

(51) Int. Cl.

| | |
|---|---|
| *G06N 20/20* | (2019.01) |
| *G06N 5/04* | (2023.01) |
| *G16B 25/00* | (2019.01) |
| *G06F 18/2433* | (2023.01) |
| *G06F 18/214* | (2023.01) |
| *G06F 18/21* | (2023.01) |
| *G06F 18/243* | (2023.01) |
| *G06N 5/01* | (2023.01) |
| *G06V 10/56* | (2022.01) |
| *G06V 10/764* | (2022.01) |
| *G06V 10/77* | (2022.01) |
| *G06V 10/774* | (2022.01) |
| *G06V 10/98* | (2022.01) |
| *G06V 20/69* | (2022.01) |
| *G01N 21/64* | (2006.01) |

(52) U.S. Cl.
CPC ........... *G06V 20/698* (2022.01); *G16B 25/00* (2019.02); *G01N 21/6428* (2013.01); *G01N 2021/6439* (2013.01); *G06T 2207/10064* (2013.01); *G06T 2207/20028* (2013.01); *G06T 2207/20081* (2013.01); *G06T 2207/20192* (2013.01); *G06T 2207/30072* (2013.01); *G06T 2207/30168* (2013.01)

(56) References Cited

U.S. PATENT DOCUMENTS

| | | | | |
|---|---|---|---|---|
| 2022/0012879 A1* | 1/2022 | De Poly | | A61B 5/4848 |
| 2022/0091923 A1* | 3/2022 | O'Toole | | G06N 20/20 |
| 2022/0114593 A1* | 4/2022 | Johnson | | G06K 9/6256 |

FOREIGN PATENT DOCUMENTS

| | | | |
|---|---|---|---|
| WO | 2018140014 A1 | 8/2018 | |
| WO | 2020081659 A1 | 4/2020 | |
| WO | WO-2021195697 A1 * | 10/2021 | |
| WO | PCT/US2022/014449 | 1/2022 | |
| WO | PCT/US2022/27114 | 4/2022 | |

OTHER PUBLICATIONS

U.S. Appl. No. 17/332,904, filed May 27, 2021, US-2021-0375398-A1, Dec. 2, 2021, Pending.
U.S. Appl. No. 17/548,424, filed Dec. 10, 2021, Pending.
PCT/US2021/015906, Jan. 29, 2021, WO2021155291, Aug. 5, 2021, Pending.
PCT/US2021/034965, May 28, 2021, WO2021243274, Dec. 2, 2021, Pending.
Chang et al., Wafer defect inspection by neural analysis of region features, journal of intelligent manufacturing, kluwer academic publishers, BO, vol. 22, No. 6, dated Dec. 23, 2009, pp. 953-964, 12 pages.
Hongxiang et al., The impact of padding on image classification by using pre-trained convolutional neural networks, Advances in databases and information Systems; [lecture notes in computer science], springer international publishing, vol. 11752 Chapter31, No. 558, dated Sep. 2, 2019, pp. 337-344 , 8 pages.
Muhammad et al., A Deep Convolutional Neural Network for Wafer defect identification on an imbalanced dataset in semiconductor manufacturing processes, IEEE transactions on semiconductor manufacturing, IEEE service center, vol. 33, No. 3, May 12, 2020 (May 12, 2020),pp. 436-444, 9 pages.
Takahashi et al., Data Augmentation using Random Image Cropping and Patching for Deep CNNs, Cornell.
He et al., Deep Residual Learning for Image Recognition, in Proc. of CVPR, 2016.

Simonyan et al., Very Deep Convolutional Networks For Large-Scale Image Recognition, ICLR 2015, dated Apr. 10, 2015, 14 pages.
Deng et al., ImageNet: A large-scale hierarchical image database, published in proceedings of IEEE Conference on Computer Vision and Pattern Recognition, dated Jun. 20-25, 2009, pp. 248-255, 8 pages.
Gonzalez et al., Section 10.3.3 Optimum Global Thresholding Using Otsu's Method, Digital Image Processing, Third edition, Pearson Prentice Hall, 2008, 7 pages.
Ilumina, Evaluation of Infinium Genotyping Assay Controls Training Guide, dated Jan. 1, 2012, 28 pages.
Huang et. al., Auto-validation of fluorescent primer extension genotyping assay using signal clustering and neural networks, BMC Bioinformatics, dated Apr. 2, 2004, 10 pages.
Illumina, GenomeStudio Genotyping Module v1.0 User Guide—An Integrated Platform for Data Visualization and Analysis, dated 2005-2008, 181 pages.
Illumina, Infinum Assay—Lab Setup and Procedures Guide, dated 2019, 37 pages.
Dunning et al., BeadArray expression analysis using Bioconductor, dated Nov. 5, 2019, 39 pages.
Poulsen et al., Investigation of Parameters that Affect the Success Rate of Microarray-Based Allele-Specific Hybridization Assays, PLOS One, vol. 6—Issue 3, dated Mar. 2011, 11 pages.
Illumina, Evaluation of Infinium Genotyping Assay Controls and Transcript, 4 pages. Retrieved on Jan. 24, 2020. Retrieved from the internet [URL: https://support.illumina.com/content/dam/illumina-support/courses/eval-inf-controls/story.html ].
Dunning et al., Quality Control and Low-Level Statistical Analysis of Illumina Beadarrays, REVSTAT—Statistical Journal, vol. 4, No. 1, dated Mar. 2006, 30 pages.
Smith et al., BeadDataPackR: A Tool to Facilitate the Sharing of Raw Data from Illumina BeadArray Studies, Cancer Informatics, vol. 9, dated 2010, 11 pages.
Kuhn et al., A novel, high-performance random array platform for quantitative gene expression profiling, Genome Research, vol. 14, dated 2004, 10 pages.
Dunning et al., Analysis of Bead-level Data Using BeadArray, dated Oct. 17, 2016, 14 pages.
Ritchie et al., BeadArray Expression Analysis Using Bioconductor, PLOS Computational Biology—vol. 7, No. 12, dated Dec. 31, 2011, 11 pages.
Gonzalez et. al., Digital Image Processing, Third edition, Pearson Prentice Hall, 2008, 977 pages.
Otsu, A Threshold Selection Method from Gray-Level Histograms, IEEE Transactions on Systems, Man and Cybernetics, vol. SMC-9, No. 1, dated Jan. 1979, 5 pages.
Turk et. al., Face Recognition Using Eigenfaces, IEEE Computer Society Conference on Computer Vision and Pattern Recognition, dated 1991, 6 pages, retrieved on Nov. 25, 2009. Retrieved from the internet [URL: https://ieeexplore.ieee.org/document/139758 ].
Navarette et. al., Comparative Study between Different Eigenspace-Based Approaches for Face Recognition, Advances in Soft Computing—AFSS 2002, dated Jan. 2002, 7 pages.
Faruqe et. al., Face Recognition using PCA and SVM, IEEE, dated Sep. 2009, 6 pages, retrieved on Dec. 2, 2019. Retrieved from the internet [URL: https://www.researchgate.net/publication/224599198 ].
Huang et al., Auto-validation of fluorescent primer extension genotyping assay using signal clustering and neural networks, BMC Bioinformatics, Biomed Central, London, GB, vol. 5, No. 1, dated Apr. 2, 2004. Section "Review by the neural network". Section "Methods", figures 1-4.
Poplin et al., A universal SNP and small-indel variant caller using deep neural networks, Nature Biotechnology, dated Sep. 24, 2018, 10 pages.
Bertolini, et al., Combined use of principal component analysis and random forests identify population-informative single nucleotide polymorphisms: application in cattle breeds, Journal of Animal Breeding and Genetics, vol. 132, No. 5, dated Mar. 17, 2015, pp. 346-356, 11 pages.

(56) References Cited

OTHER PUBLICATIONS

PCT/US2021/015906 Partial Search Report and Invitation to pay, dated Apr. 21, 2021, 14 pages.
PCT/US2021/015906 International Search Report and Written Opinion, dated Jul. 15, 2021, 30 pages.

* cited by examiner

515

Bad Process Cycle Image – Hybridization (Hyb) Failure (2/2)

| | unhealthy (new) | | | hyb (new) | hyb (new) | | | hyb (new) | | | |
|---|---|---|---|---|---|---|---|---|---|---|---|
| 99.892 | 99.251 | 99.867 | 99.779 | 99.812 | 99.92 | 99.899 | 99.908 | 99.582 | 99.93 | 99.92 | 99.901 |
| R01C02 | R02C02 | R03C02 | R04C02 | R05C02 | R06C02 | R07C02 | R08C02 | R09C02 | R10C02 | R11C02 | R12C02 |
| R01C01 | R02C01 | R03C01 | R04C01 | R05C01 | R06C01 | R07C01 | R08C01 | R09C01 | R10C01 | R11C01 | R12C01 |
| 99.899 | 99.579 | 9.931 | 99.903 | 99.916 | 99.934 | 99.907 | 99.925 | 99.874 | 99.486 | 99.905 | 99.865 |
| | | | | hyb (new) | | | | | | | |

MACHINE LEARNING-BASED ROOT CAUSE ANALYSIS OF PROCESS CYCLE IMAGES

PRIORITY APPLICATION

This application claims the benefit of U.S. Provisional patent Application No. 62/968,950, entitled "MACHINE LEARNING-BASED ROOT CAUSE ANALYSIS OF PROCESS CYCLE IMAGES," filed Jan. 31, 2020. The provisional application is incorporated by reference for all purposes.

FIELD OF THE TECHNOLOGY DISCLOSED

The technology disclosed relates to classification of images for evaluation and root cause failure analysis of production processes.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Genotyping is a process that can take multiple days to complete. The process is vulnerable to both mechanical and chemical processing errors. Collected samples for genotyping are extracted and distributed in sections and areas of image generating chips. The samples are then chemically processed through multiple steps to generate fluorescing images. The process generates a quality score for each section analyzed. This quality cannot provide insight into the root cause of failure a low-quality process. In some cases, a failed section image still produces an acceptable quality score.

Accordingly, an opportunity arises to introduce new methods and systems to evaluate section images and determine root causes of failure analysis during production genotyping.

BRIEF DESCRIPTION OF THE DRAWINGS

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIGS. 5A and 5B present examples of failed section images due to hybridization failure during genotyping process.

FIG. 5E presents examples of failed section images due to offset failures.

FIGS. 5G and 5H presents examples of failed section images due to reagent flow failure.

DETAILED DESCRIPTION

Figure 1:
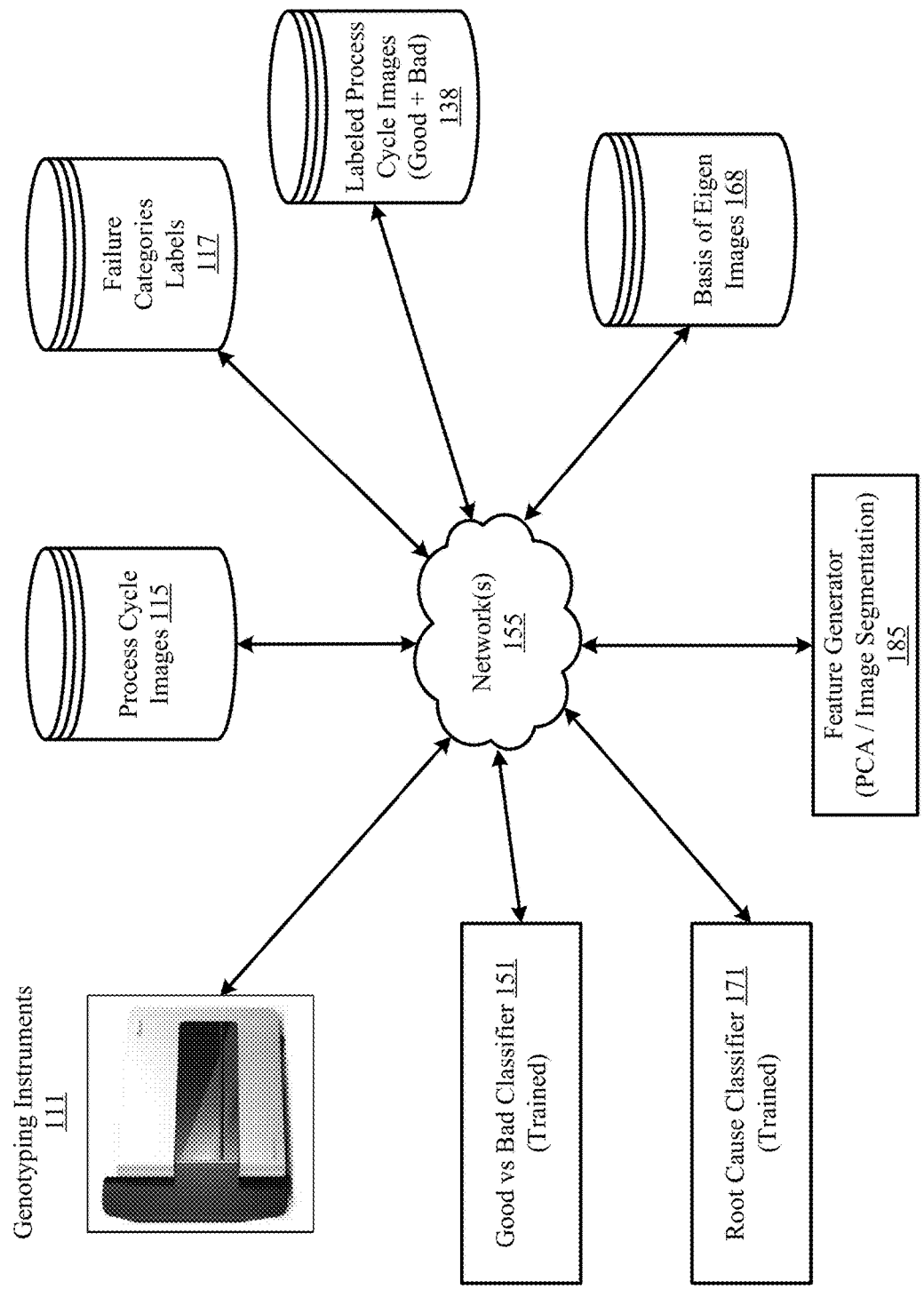
FIG. 1 shows an architectural level schematic of a system in which process cycle images from genotyping instruments are classified and root cause of bad images is determined.

The following discussion is presented to enable any person skilled in the art to make and use the technology disclosed, and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein.

INTRODUCTION

The technology disclosed applies vision systems and image classification for evaluation and root cause failure analysis of production genotyping. Two distinct approaches are described, one involving Eigen images and the other based on thresholding by area. Principal components analysis (PCA) and non-negative matrix factorization (NMF) are among the techniques disclosed. Other dimensionality reduction techniques that can applied to images include, independent component analysis, dictionary learning, sparse principal component analysis, factor analysis, mini-batch K-means. Variations of image decomposition and dimensionality reduction techniques can be used. For example, PCA can be implemented using singular value decomposition (SVD) or as kernel PCA. Outputs from these techniques are given as inputs to classifiers. Classifiers applied can include random forest, K-nearest neighbors (KNN), multinomial logistic regression, support vector machines (SVM), gradient boosted trees, Naïve Bayes, etc. As larger bodies of labeled images become available, convolutional neural networks such as ImageNet could also be used.

This production process is vulnerable to both mechanical and chemical processing errors. Collected samples are extracted, distributed in sections and areas of BeadChips, then chemically processed through multiple steps to generate fluorescing images. A final fluorescing image, or even intermediate fluorescing images, can be analyzed to monitor production and conduct failure analysis.

The vast majority of production analyses are successful. The failed analyses currently are understood to fit in five categories plus a residual failure category. The five failure categories are hybridization or hyb failures, spacer shift failures, offset failures, surface abrasion failures and reagent flow failures. The residual category is unhealthy patterns due to mixed effects, unidentified causes and weak signals. In time, especially as root cause analysis leads to improved production, more and different causes may be identified.

The first image processing technology applied to quality control and failure analysis is evolved from facial recognition by Eigen face analysis. From tens of thousands of labeled images, a linear basis of 40 to 100 or more image components was identified. One approach to forming an Eigen basis was principal component analysis (PCA) followed by rank ordering of components according to a measure of variability explained. It was observed that 40 components explained most of the variability. Beyond 100 components, the additional components appeared to reflect patterns of noise or natural variability in sample processing. The number of relevant components is expected to be impacted by image resolution. Here, resolution reduction was applied so that sections of the image generating chip were analyzed at a resolution of 180×80 pixels. This was sufficient resolution to distinguish successful from unsuccessful production and then to classify root causes of failure among six failure categories. No formal sensitivity analysis was applied, but it is expected that slightly lower resolution images also would work and that images with 4 to 22 times this resolution could be processed in the same way, though with increased computational expense. Each image to be analyzed by Eigen image analysis is represented as a weighted linear combination of basis images. Each weight for the ordered set of basis components is used as a feature for training a classifier. For instance, in one implementation, 96 weights for components of labelled images were used to train random forest classifiers. A random forest classifier with 200 trees and a depth of 20 worked well. Two tasks were performed by the random forest classifiers: separation of successful and unsuccessful production images, then root cause analysis of the unsuccessful production images. This two-stage classification was selected due to the dominance of successful production runs, but a one-stage classification also could be used.

The second image processing technology applied involved thresholding of image areas. A production image of a section of an image generating chip captures several physically separated areas. Structures that border the section and that separate physical areas of the section are visible in a production image. The thresholding strategy involves separating the active areas from the border structures and then distinguishing among the separated areas. Optionally, the structures that separate the physical areas also can be filtered out of the image. At least the active areas are subject to thresholding for luminescence. The thresholding determines how much of an active area is producing a desired signal strength. Each active area is evaluated after thresholding for success or failure. A pattern of failures among areas and sections of an image generating chip can be further evaluated for root cause classification.

Processing of production images to detect failed production runs and determine root causes, can be performed immediately during production, more quickly even than results are read from the image generating chip and judged for quality. This image processing can be done more quickly because shrinking an image by 20 times on a side greatly reduces computational requirements and direct processing of a reduced resolution image does not require correlation of individual glowing pixels in an area to individual probes. Quick turnaround of root cause analysis can be used to correct upstream processes before chemicals and processing time are wasted.

Environment

We describe a system for early prediction of failure in genotyping systems. Genotyping is the process of determining differences in genetic make-up (genotype) of an individual by examining the individual's DNA sequence using biological assays and comparing it to a reference sequence. Genotyping enables researchers to explore genetic variants such as single nucleotide polymorphisms (SNPs) and structural changes in DNA. The system is described with reference to FIG. 1 showing an architectural level schematic of a system in accordance with an implementation. Because FIG. 1 is an architectural diagram, certain details are intentionally omitted to improve the clarity of the description. The discussion of FIG. 1 is organized as follows. First, the elements of the figure are described, followed by their interconnection. Then, the use of the elements in the system is described in greater detail.

FIG. 1 includes the system 100. This paragraph names labeled parts of system 100. The figure illustrates genotyping instruments 111, a process cycle images database 115, a failure categories labels database 117, a labeled process cycle images database 138, a trained good vs. bad classifier 151, a basis of Eigen images database 168, a trained root cause classifier 171, a feature generator 185, and a network(s) 155.

The technology disclosed applies to a variety of genotyping instruments 111, also referred to as genotyping scanners and genotyping platforms. The network(s) 155 couples the genotyping instruments 111, the process cycle images database 115, the failure categories labels database 117, the labeled process cycle images database 138, the trained good vs. bad classifier 151, the basis of Eigen images database 168, the trained root cause classifier 171, and the feature generator 185, in communication with one another.

The genotyping instruments can include Illumina's BeadChip imaging systems such as ISCAN™ system. The instrument can detect fluorescence intensities of hundreds to millions of beads arranged in sections on mapped locations on image generating chips. The genotyping instruments can include an instrument control computer that controls various aspects of the instrument, for example, laser control, precision mechanics control, detection of excitation signals, image registration, image extraction, and data output. The genotyping instruments can be used in a wide variety of physical environments and operated by technicians of varying skills levels. The sample preparation can take two to three days and can include manual and automated handling of samples.

Figure 3:
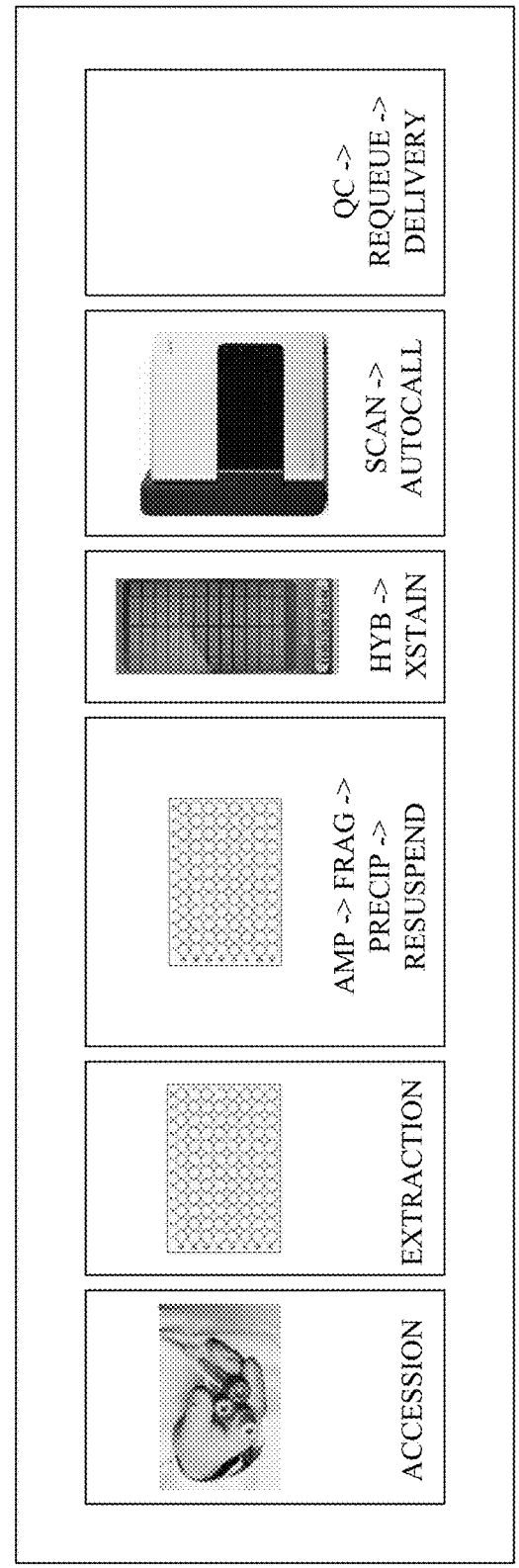
FIG. 3 presents process steps for an example genotyping process.

We illustrate process steps of an example genotyping process 300 in FIG. 3. This example genotyping process is referred to as Illumina's INFINIUM™ Assay Workflow. The process is designed to investigate many SNPs at extensive levels of loci multiplexing. Using a single bead type and dual-color (such as red and green) channel approach, the process scales genotyping from hundreds to millions of SNPs per sample. The process starts with accession and extraction of DNA samples. The process can operate with relatively low input sample such as 200 ng which can assay millions of SNP loci. The samples are amplified. The amplification process can take from a few hours to overnight to complete. The amplified sample undergoes controlled enzymatic fragmentation. This is followed by alcohol precipitation and resuspension. The image generating chip is prepared for hybridization in a capillary flow-through chamber. The samples are then applied to prepared image generating chips and incubated overnight. During this overnight hybridization, the samples anneal to locus-specific 50-mers covalently linked to up to millions of bead types. One bead type corresponds to each allele per SNP locus. The allelic specificity is conferred by enzymatic base extension followed by fluorescent staining. The genotyping instrument or scanner (such as ISCAN™ system) detects the fluorescence intensities of the beads and performs genotype calling.

In one example, the results of the genotyping are presented using a metric called "Call Rate". This metric represents the percentage of genotypes that were correctly scanned on the image generating chip. A separate call rate is reported per section of the image generating chip. A threshold can be used to accept or reject the results. For example, a call rate of 98% or more can be used to accept the genotyping results for a section. A different threshold value such as lower than 98% or higher than 98% can be used. If the call rate for a section is below the threshold, the genotyping process is considered as failed. The genotyping process can span over many days and is therefore, expensive to repeat. Failures in genotyping process can occur due to operational errors (such as mechanical or handling errors) or chemical processing errors.

The genotyping systems can provide process cycle images of the image generating chip sections along with their call rates upon completion of the genotyping process. The technology disclosed can process these section images to classify whether the genotyping process is successful (good image of section) or not successful (bad or failed image of section). The technology disclosed can further process the bad or failed images to determine a category of failure. Currently, the system can classify the failed images in one of the six failure categories: hybridization or hyb failures, spacer shift failures, offset failures, surface abrasion failures, reagent flow failures and overall unhealthy images due to mixed effects, unknown causes, weak signals etc. In time, especially as root cause analysis leads to improved production, more and different causes may be identified.

We now refer to FIG. 1 to provide description of remaining components of the system 100. The failure category labels for the six failure types can be stored in the failure categories labels database 117. A training dataset of labeled process image cycles is stored in the database 138. The labeled training examples can comprise of successful (good) and unsuccessful (bad) process cycle images. The unsuccessful process cycle images are labeled as belonging to one of the six failure categories listed above. In one implementation, the training database 138 comprises of at least 20,000 training examples. The size of the training database can increase, as more labeled image data is collected from laboratories using the genotyping instruments.

The technology disclosed includes two independent image processing techniques to extract features from process cycle images. The feature generator 185 can be used to apply one of the two techniques to extract features from process cycle images for input to machine learning models. The first image processing technique is evolved from facial recognition by Eigen face analysis. A relatively small number of linear basis such as from 40 to 100 or more image components are identified from tens of thousands of labeled images. One approach to form Eigen basis is Principal Component Analysis (PCA). The production cycle images are represented as a weighted linear combination of basis images for input to classifiers. For example, in one implementation, 96 weights for components of labeled images are used to train the classifiers. The basis of Eigen images can be stored in the database 168.

The second image processing technique to extract features involves thresholding of section images. A production image of a section of an image generating chip captures several physically separated areas. Structures that border the section and that separate physical areas of the section are visible in a production image. Thresholding technique determines how much of an active area is producing a desired signal strength. The output from thresholding technique can be given as input to a classifier to distinguish good images from bad images. A pattern of failures among areas and sections of an image generating chip can be further evaluated for root cause analysis.

The image features of production images generated by the feature generator 185 are given as input to trained classifiers 151 and 171. Two types of classifiers are trained. A good vs. bad classifier can predict successful and unsuccessful production images. A root cause analysis classifier can predict failure categories of unsuccessful images. One example of classifiers used by the technology disclosed includes random forest classifiers. Other examples of classifiers that can be applied include K-nearest neighbors (KNN), multinomial logistic regression, and support vector machines. As larger bodies of labeled images become available, convolutional neural networks (CNNs) can be also be used.

Completing the description of FIG. 1, the components of the system 100, described above, are all coupled in communication with the network(s) 155. The actual communication path can be point-to-point over public and/or private networks. The communications can occur over a variety of networks, e.g., private networks, VPN, MPLS circuit, or Internet, and can use appropriate application programming interfaces (APIs) and data interchange formats, e.g., Representational State Transfer (REST), JavaScript Object Notation (JSON), Extensible Markup Language (XML), Simple Object Access Protocol (SOAP), Java Message Service (JMS), and/or Java Platform Module System. All of the communications can be encrypted. The communication is generally over a network such as the LAN (local area network), WAN (wide area network), telephone network (Public Switched Telephone Network (PSTN), Session Initiation Protocol (SIP), wireless network, point-to-point network, star network, token ring network, hub network, Internet, inclusive of the mobile Internet, via protocols such as EDGE, 3G, 4G LTE, Wi-Fi and WiMAX. The engines or system components of FIG. 1 are implemented by software running on varying types of computing devices. Example devices are a workstation, a server, a computing cluster, a blade server, and a server farm. Additionally, a variety of authorization and authentication techniques, such as username/password, Open Authorization (OAuth), Kerberos, Secured, digital certificates and more, can be used to secure the communications.

Feature Generator—System Components

Figure 2:
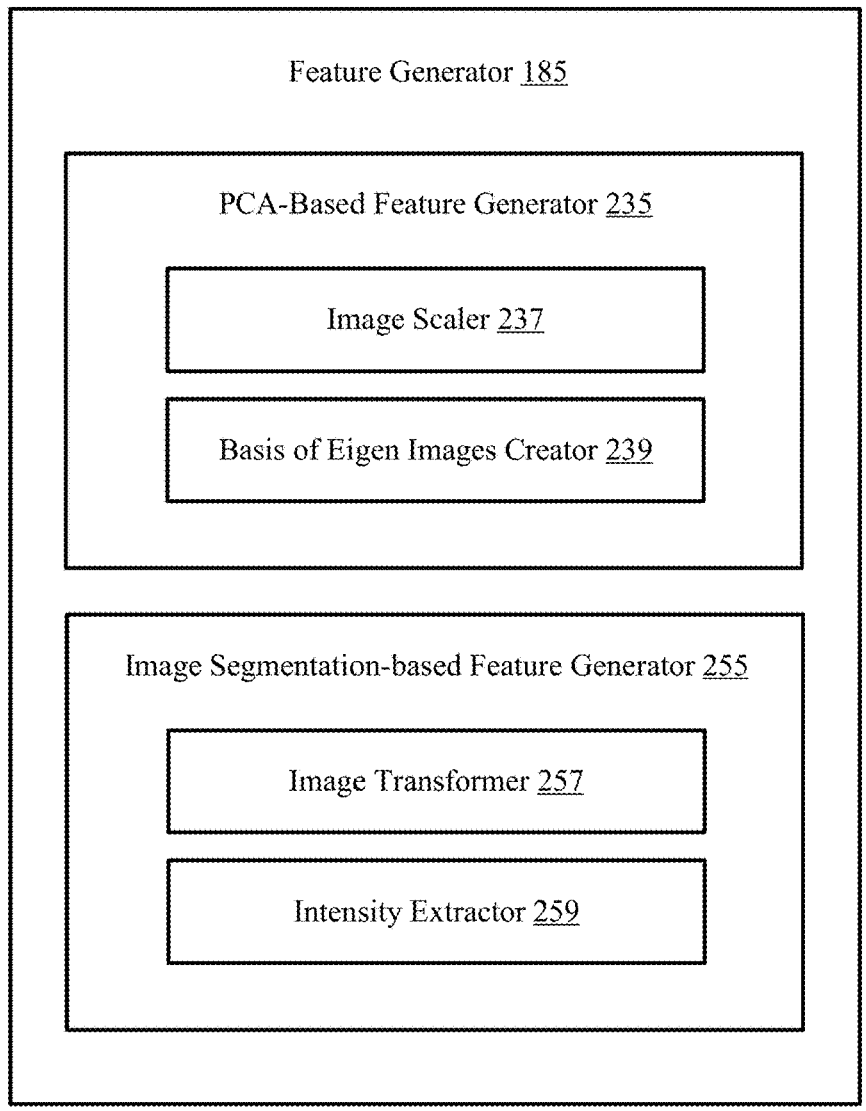
FIG. 2 illustrates subsystem components of feature generator of FIG. 1.

FIG. 2 is a high-level block diagram 200 of components of feature generator 185. These components are computer implemented using a variety of different computer systems as presented below in description of FIG. 11. The illustrated components can be merged or further separated, when implemented. The feature generator 185 consists of two high-level components implementing the two image processing techniques: Principal Component Analysis or PCA-based feature generator 235 and image segmentation-based feature generator 255. The PCA-based feature generator comprises of an image scaler 237 and a basis of Eigen images creator 239. The image segmentation-based feature generator 255 comprises of an image transformer 257 and an intensity extractor 259. In the following sections, we present further details of the implementation of these components.

PCA-Based Feature Generator

The first image processing technique is evolved from facial recognition by Eigen face analysis. One approach to forming an Eigen basis is principal component analysis (PCA). The PCA-based feature generator 235 applies PCA to resized process images. The image scaler component 237 resizes (or rescales) the process cycle images. Scaling reduces size of process images so that they can be processed in a computationally efficient manner by the basis of Eigen images creator component 239. We present details of these components in the following sections.

Image Scaler

Higher resolution images obtained from genotyping instruments or scanners can require more computational resources to process. The images obtained from genotyping scanners are resized by the image scaler 237 so that images of sections of image generating chips are analyzed at a reduced resolution of 180×80 pixels. In one instance, images of the sections obtained from the scanner are at a resolution of 3600×1600 pixels and a 20 times reduction of the resolution is applied to resize the images. This is sufficient resolution to distinguish successful production images from unsuccessful production images and then to classify root causes of failure among six failure categories. Images rescaled from 4 to 25 times the original resolution can be processed in the same way.

The technology disclosed can apply a variety of interpolation techniques to reduce the size of the production images. In one implementation, bilinear interpolation is used to reduce size of the section images. Linear interpolation is a method of curve fitting using linear polynomials to construct new data points with the range of a discrete set of known data points. Bilinear interpolation is an extension of linear interpolation for interpolating functions of two variables (e.g., x and y) on a two-dimensional grid. Bilinear interpolation is performed using linear interpolation first in one direction and then again in a second direction. Although each step is linear in the sampled values and in the position, the interpolation as a whole is not linear but rather quadratic in the sample location. Other interpolation techniques can also be used for reducing the size of the section images (rescaling) such as nearest-neighbor interpolation and resampling using pixel area relation.

Basis of Eigen Images Creator

The first image processing technique applied to section images to generate input features for classifiers is evolved from facial recognition by Eigen face analysis. From tens of thousands of labeled images, a linear basis of 40 to 100 or more image components is identified. One approach to forming the basis of Eigen images is principal component analysis (PCA). A set B of elements (vectors) in a vector space Vis called a basis, if every element of V may be written in a unique way as a linear combination of elements of B. Equivalently, B is a basis if its elements are linearly independent, and every element of V is a linear combination of elements of B. A vector space can have several bases. However, all bases have the same number of elements, called the dimension of the vector space. In our technology, the basis of the vector space are Eigen images.

PCA is often used to reduce the dimensions of a d-dimensional dataset by projecting it onto a k-dimensional subspace where k<d. For example, a resized labeled image in our training database describes a vector of dimension d=14,400-dimensional space (180×80 pixels). In other words, the image is a point in 14,400-dimensional space. Eigen space-based approaches approximate the image vectors with lower dimension feature vectors. The main supposition behind this technique is that the image space (given by the feature vectors) has a lower dimension than the image space (given by the number of pixels in the image) and that the recognition of images can be performed in this reduced space. Images of sections of image generating chips, being similar in overall configuration, will not be randomly distributed in this huge space and thus can be described by a relatively low dimensional subspace. The PCA technique finds vectors that best account for the distribution of section images within the entire image space. These vectors define the subspace of images which is also referred to as "image space". In our implementation, each vector describes a 180×80 pixels image and is a linear combination of images in the training data. In the following text, we present details of how principal component analysis (PCA) can be used to create the basis of Eigen images.

The PCA-based analysis of labeled training images can comprise of the following five steps.

Step 1: Accessing Multi-Dimensional Correlated Data

The first step in application of PCA is to access high dimensional data. In one instance, we used as training data 20,000 labeled images. Each image was resized to 180×80 pixels resolution and represented as a point in a 14,400-dimensional space, one dimension per pixel. This technique can handle images of higher resolution or lower resolution than specified above. The size of the training data set is expected to increase as we collect more labeled images from laboratories.

Step 2: Standardization of the Data

Standardization (or Z-score normalization) is the process of rescaling the features so that they have properties of a Gaussian distribution with mean equal to zero or $\mu=0$ and standard deviation from the mean equal to 1 or $\sigma=1$. Standardization is performed to build features that have similar ranges to each other. Standard score of an image can be calculated by subtracting the mean (image) from the image and dividing the result by standard deviation. As PCA yields a feature subspace that maximizes the variance along the axes, it helps to standardize the data so that it is centered across the axes.

Step 3: Computing Covariance Matrix

The covariance matrix is a d×d matrix of d-dimensional space where each element represents covariance between two features. The covariance of two features measures their tendency to vary together. The variation is the average of the squared deviation of a feature from its mean. Covariance is the average of the products of deviations of feature values from their means. Consider feature k and feature j. Let {x(1, j), x(2, j), ... x(i, j)} be a set of i examples of feature j, and let {x(1, k), x(2, k), ... x(i, k)} be a set of i examples of feature k. Similarly, let $\bar{x}_j$ be the mean of feature j and $\bar{x}_k$ be the mean of feature k. The covariance of feature j and feature k is calculated as follows:

$$\sigma_{jk} = \frac{1}{n-1} \sum_{i=1}^{n} (x(i, j) - \bar{x}_j)(x(i, k) - \bar{x}_k) \quad (1)$$

We can express the calculation of the covariance matrix via the following matrix equation:

$$\sum = \frac{1}{n-1}\left((X - \bar{x})^T (X - \bar{x})\right) \quad (2)$$

Where the mean vector can be represented as:

$$\bar{x} = \frac{1}{n} \sum_{i=1}^{n} x_i.$$

The mean vector is a d-dimensional vector where each value in this vector represents the sample mean of a feature column in the training dataset. The covariance value $\sigma_{jk}$ can vary between the—$(\sigma_{ij})(\sigma_{ik})$ i.e., inverse linear correlation to $+(\sigma_{ij})(\sigma_{ik})$ linear correlation. When there is no dependency between two features the value of $\sigma_{jk}$ is zero.

Step 4: Calculating Eigenvectors and Eigenvalues

The eigenvectors and eigenvalues of a covariance matrix represent the core of PCA. The eigenvectors (or principal components) determine the directions of the new feature space and the eigenvalues determine their magnitudes. In other words, eigenvalues explain the variance of the data along the axes of the new feature space. Eigen decomposition is a method of matrix factorization by representing the matrix using its eigenvectors and eigenvalues. An eigenvector is defined as a vector that only changes by a scalar when linear transformation is applied to it. If A is a matrix that represents the linear transformation, v is the eigenvector and λ is the corresponding eigenvalue, it can be expressed as Av=λv. A square matrix can have as many eigenvectors as it has dimensions. If we represent all eigenvectors as columns of a matrix V and corresponding eigenvalues as entries of a diagonal matrix L, the above equation can be represented as AV=VL. In case of a covariance matrix all eigenvectors are orthogonal to each other and are the principal components of the new feature space.

Step 5: Using Explained Variance to Select Basis for Eigen Images

The above step can result in 14,400 principal components for our implementation which is equal to the dimension of the feature space. An eigenpair consists of the eigenvector and the scalar eigenvalue. We can sort the eigen pairs based on eigenvalues and use a metric referred to as "explained variance" to create a basis of eigen images. The explained variance indicates how much information (or variance) can be attributed to each of the principal component. We can plot the results of explained measure values on a two-dimensional graph. The sorted principal components are represented along x-axis. A graph can be plotted indicating cumulative explained variance. The first in components that represent a major portion of the variance can be selected.

In our implementation, the first 40 components expressed a high percentage of the explained variance, therefore, we selected the first 40 principal components to form bases of our new feature space. In other implementations, 25 to 100 principal components or more than 100 principal components, up to 256 or 512 principal components, can be selected to create a bases of Eigen images. Each production image to be analyzed by Eigen image analysis is represented as a weighted linear combination of the basis images. Each weight of the ordered set of basis components is used as a feature for training the classifier. For instance, in one implementation, 96 weights for components of labeled images were used to train the classifier.

The technology disclosed can use other image decomposition and dimensionality reduction techniques. For example, non-negative matrix factorization (NMF) which learns a parts-based representation of images as compared to PCA which learns complete representations of images. Unlike PCA, NMF learns to represent images with a set of basis images resembling parts of images. NMF factorizes a matrix X into two matrices W and H, with the property that all three matrices have no negative elements. Let us assume that matrix X is set-up so that there are n data points (such as images of sections on image generating chips) each with p dimensions (e.g., 14,400). Thus, matrix X hasp rows and n columns. We want to reduce the p dimensions to r dimensions or in other words create a rank r approximation. NMF approximates matrix X as a product of two matrices: W (p rows and r columns) and H (r rows and n columns).

The interpretation of matrix W is that each column is a basis element. By basis element we mean some component that is present in the n original data points (or images). These are the building blocks from which we can reconstruct approximations to all of the original data points or images. The interpretation of matrix H is that each column gives the coordinates of a data point in the basis matrix W. In other words, it tells us how to reconstruct an approximation to the original data point from a linear combination of the building blocks in matrix W. In case of facial images, the basis elements (or basis images) in matrix W can include features such as eyes, noses, lips, etc. The columns of matrix H indicate which features are present in which image.

Image Segmentation-Based Feature Generator

The second image processing technique to extract features from process cycle images is based on thresholding of image areas. The image segmentation-based feature generator 255 applies thresholding by first segmenting images of sections of an image generating chip using image segmentor 257 and then extracting intensity of active areas or regions of interest of a section image. The thresholding determines how much of an active area is producing a desired signal strength.

An image generating chip can comprise of multiple sections such as 24, 48, 96 or more, organized into rows and columns. This design enables processing of multiple samples in one process cycle as many samples (one per section) can be processed in parallel. A section is physically separated from other sections so that samples do not mix with each other. Additionally, a section can be organized into multiple parallel regions referred to as "slots". The structures at borders of sections and slots are therefore visible in the process cycle images from genotyping scanners. We present below, details of the two components of image segmentation-based feature generator 255 that can implement techniques to transform section images for extraction of image features.

Image Transformer

The image transformer 257 applies a series of image transformation techniques to prepare the section images for extracting intensities from regions of interest. In one implementation, this process of image transformation and intensity extraction is performed by some or all of the following five steps. The image transformation converts grayscale image of a section into a binary image consisting of black and bright pixels. Average intensity values of active areas of grayscale image and binary image are given as input features to a classifier to classify the image as a healthy (good) or unhealthy (bad) image. In the following text we present details of the image transformation steps which include applying thresholding to convert the grayscale image into binary image. The process steps include applying filters to remove noise.

The first step in the image transformation process is to apply a bilateral filter to process cycle images of sections. The bilateral filter is a technique to smooth images while preserving edges. It replaces the intensity of each pixel with a weighted average of intensity values from its neighboring pixels. Each neighbor is weighted by a spatial component that penalizes distant pixels and a range component that penalizes pixels with a different intensity. The combination of both components ensures that only nearby similar pixels contribute to a final result. Thus, bilateral filter is an efficient way to smooth an image while preserving its discontinuities or edges. Other filters can be used such as median filter and anisotropic diffusion.

The second step in image transformation can be to apply thresholding to output images from step 1. In one implementation, we apply Otsu's method (Otsu, N., 1979, "A threshold selection method from gray-level histograms", IEEE Transactions on Systems, Man, and Cybernetics, Volume 9, Issue 1) that uses histogram of intensities and searches for a threshold to maximize a weighted sum of grayscale variance between pixels assigned to dark and bright intensity classes. Otsu's method attempts to maximize the between-class variance. The basic idea is that well-thresholded classes should be distinct with respect to the intensity values of their pixels and, conversely, that a threshold giving the best separation between classes in terms of their intensity values would be the best threshold. In addition, Otsu's method has the property that it is based entirely on computations performed on the histogram of an image, which is an easily obtainable one-dimensional array. For further details, refer to Section 10.3.3 of Gonzalez and Woods, "Digital Image Processing", $3^{rd}$ Edition.

The third step in image transformation is application of noise reduction Gaussian blur filter to remove speckle-like noise. Noise can contaminate the process cycle images with small speckles. Gaussian filtering is a weighted average of the intensity of adjacent positions with a weight decreasing with the spatial distance to the center position.

The fourth step in image transformation includes image morphology operations. The binary output images from third step are processed by morphological transformation to fill holes in the images. A hole maybe defined as a background region (represented by 0s) surrounded by a connected border of foreground pixels (represented by 1s). Two basic image morphology operations are "erosion" and "dilation". In erosion operation, a kernel slides (or moves) over the binary image. A pixel (either 1 or 0) in the binary image is considered 1 if all the pixels under the kernel are 1s. Otherwise, it is eroded (changed to 0). Erosion operation is useful in removing isolated 1s in the binary image. However, erosion also shrinks the clusters of is by eroding the edges. Dilation operation is the opposite of erosion. In this operation, when a kernel slides over the binary image, the values of all pixels in the binary image area overlapped by the kernel are changed to 1, if value of at least one pixel under the kernel is 1. If dilation operation is applied to the binary image followed by erosion operation, the effect is closing of small holes (represented by 0s in the image) inside clusters of 1s. The output from this step is provided as input to intensity extractor component 259 which performs the fifth step of this image transformation technique.

Intensity Extractor

The intensity extractor 259 divides section images into active areas or segments by filtering out the structures at the boundaries of sections and slots. The intensity extractor can apply different segmentations to divide section images from eight up to seventeen or more active areas. Examples of areas in a section image include four slots, four corners, four edges between corners and various vertical and horizontal lines at the borders of the section and the slots. The areas that correspond to known structures that separate active areas are then removed from the image. The image portions for remaining active areas are processed by the intensity extractor 259. Intensity values are extracted and averaged for each active area of transformed image and corresponding non-transformed image. For example, if intensity values are extracted from 17 active areas of transformed image then the intensity extractor also extracts intensity values from the same 17 active areas of the non-transformed image. Thus, a total of 34 features are extracted per section image.

In case of binary images, the average intensity of an active area can be between 1 and 0. For example, consider intensity of a black pixel is 0 and intensity of a bright (or blank) pixel is 1. If all pixels in an active area are black, then the average intensity of the active area will be 0. Similarly, if all pixels in an active area are bright then the intensity of that area will be 1. The active areas in healthy images appear as blank or bright in the binary images while black pixels represent unhealthy images. The average intensities of corresponding active areas in grayscale image are also extracted. The average intensities of active areas from both grayscale image and transformed binary image are given as input to the good vs. bad classifier. In one implementation, the classification confidence score from the classifier is compared with a threshold to classify the image as a healthy (good) image or an unhealthy (bad) image. An example of threshold value is 80%. A higher value of a threshold can result in more images classified as unhealthy.

Process Cycle Images

Figure 4:
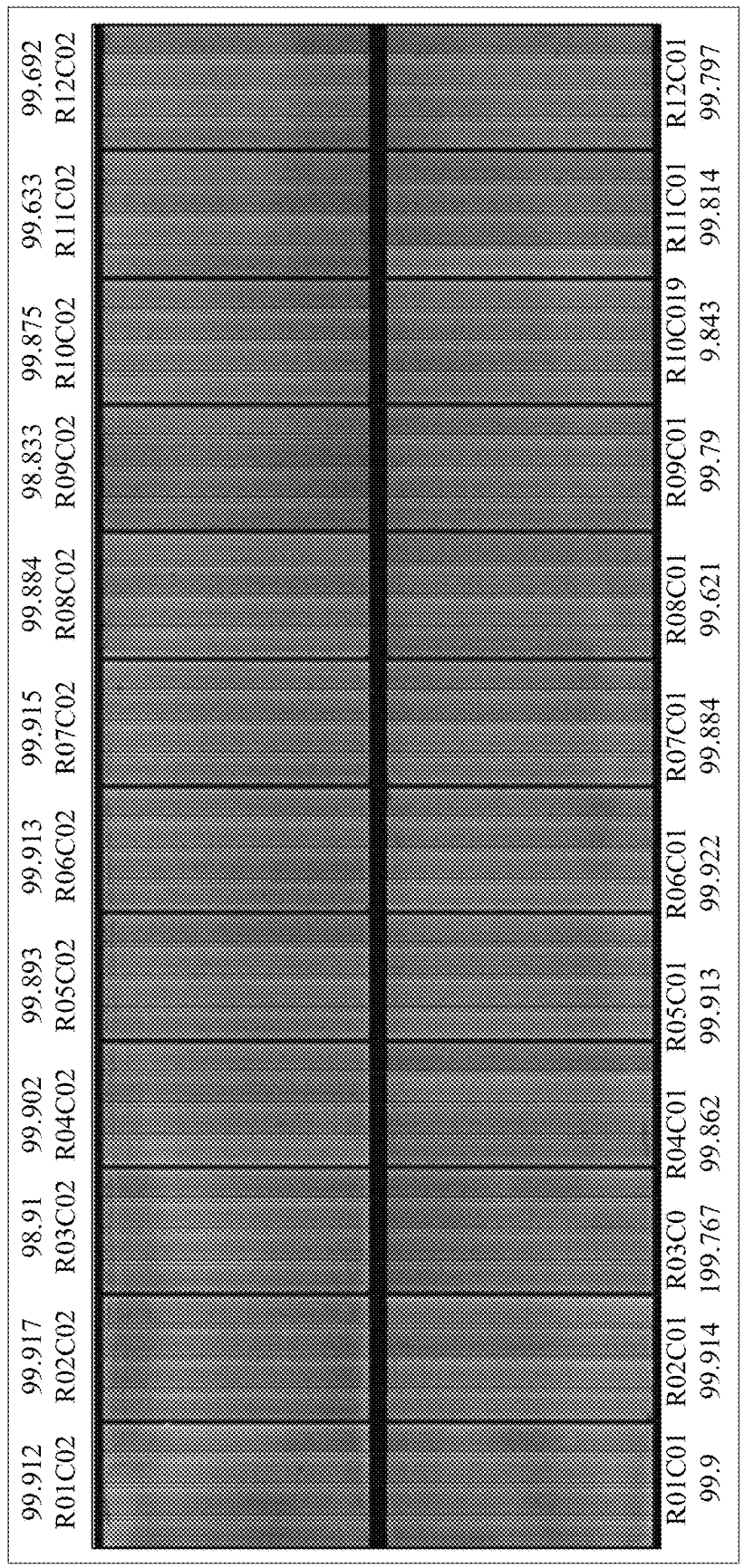
FIG. 4 presents images of sections arranged in an image generating after successful process completion.

We now present examples of successful and unsuccessful production images of sections on image generating chips. FIG. 4 is an illustration 400 of production images of 24 sections on an image generating chip. The sections are arranged in twelve rows and two columns. Each section has four slots. The illustration 400 shows section images of a successful production cycle. Image generating chips with other configurations of sections can also be used such as including 48, 96 or more sections. In the following figures, we present examples of section images of unsuccessful production cycles. The production process is vulnerable to both operational and chemical processing errors. The operational defects can be caused due to mechanical or sample handling issues. Chemical processing errors can be caused by issues in samples or chemical processing of the samples. The technology disclosed attempts to classify bad process image cycles occurring due to both operational and chemical processing errors.

Figure 5A:
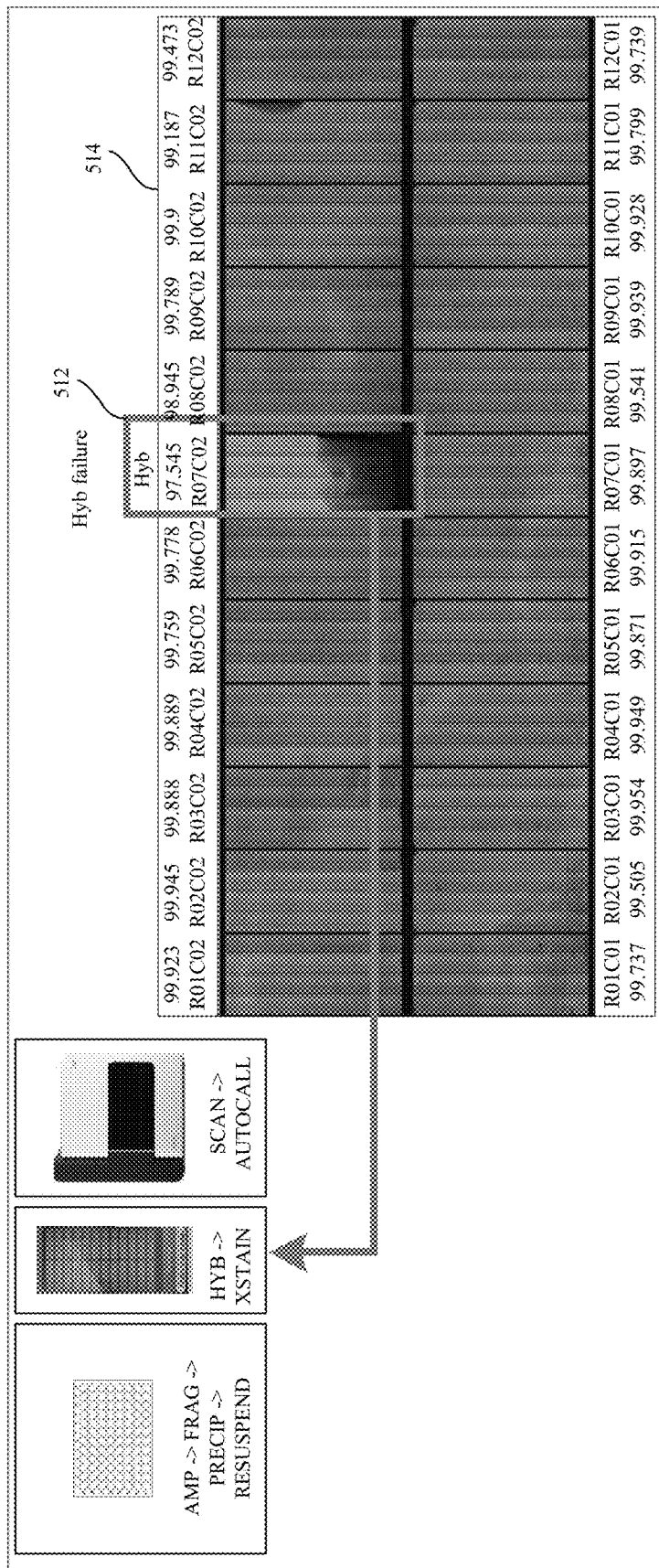

FIG. 5A shows an example 510 of a section image from an unsuccessful production cycle. The image of section 512 in second column and seventh row of the image generating chip in FIG. 5A is dark colored in bottom half portion and slightly light colored in top portion. The cause of this failure is linked to the hybridization process. Therefore, the failed image of the section is labeled as "Hyb" failure. Hybridization failures can also occur due to failures of robots that handle samples during sample preparation process on image generating chips. The call rate for this section is below the 98 percent threshold as shown in the figure. In some cases, the call rate for section from genotyping instruments can be above the pass threshold and even then, the section image can fail due to hybridization error.

It can be noted that in illustration 510, the image of section 514 at row 11 and column 2 has a dark colored region on the right wall. This may also indicate a processing issue, however, the overall call rate of this image is above the pass threshold and it is not labeled as a failed image. There is sufficient redundancy of samples on the section due to which small areas of sections with apparent failure can be ignored and may not cause errors in the results. For example, in one instance, the scanner reads fluorescence from about 700K probes on a section with a redundancy of 10. Therefore, the call rate is based on readout of about 7 million probes. We present further examples of hybridization failures in illustration 515 in FIG. 5B. Four sections on image generating chip in broken line boundaries show bad production images of sections due to hybridization failure. Note that the call rate values for these four sections are above pass threshold but images of these sections are labeled as failed due to hybridization error.

Figure 5C:
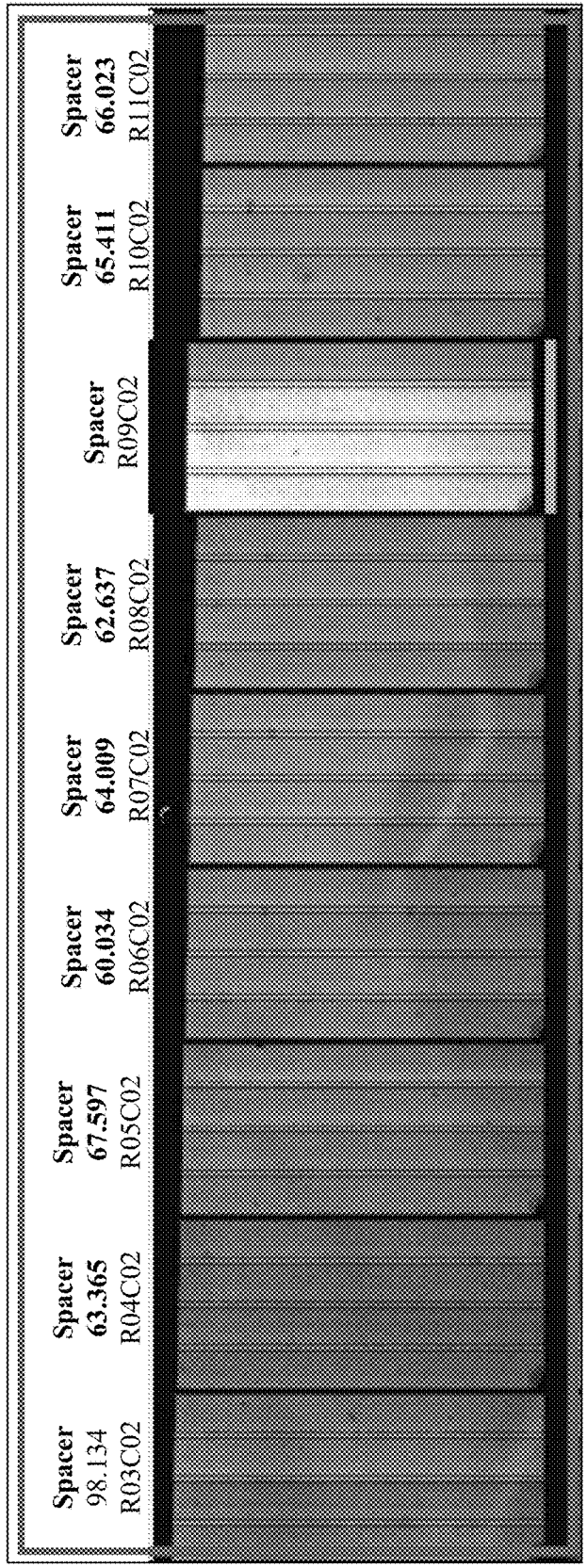
FIGS. 5C and 5D present examples of failed section images due to spacer shift failures.
Figure 5D:
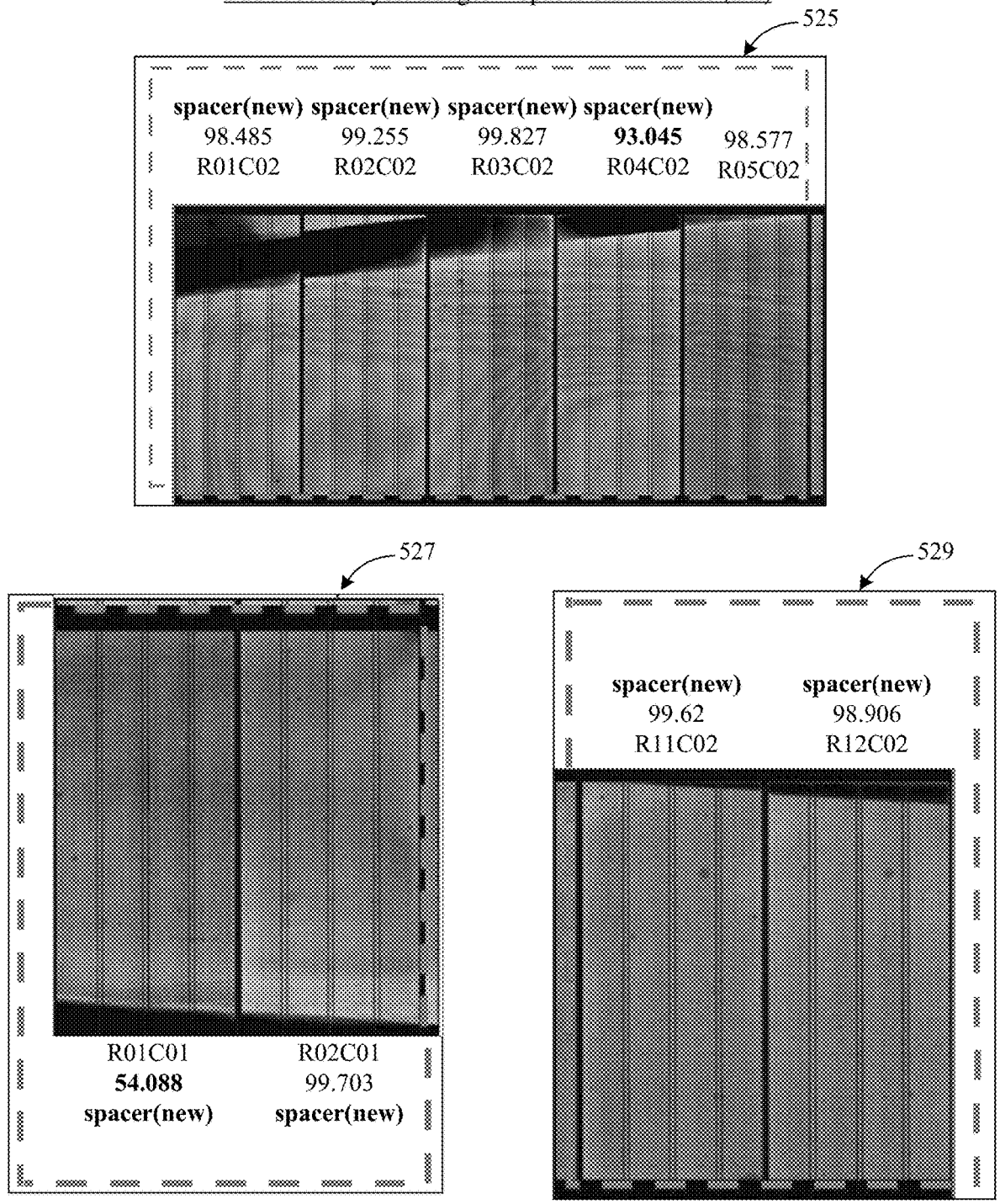

FIG. 5C presents an illustration 520 of nine section images that show unsuccessful processing due to spacer shift failure. When samples are prepared on sections on an image generating chip, a dark colored marker is placed around the sections. The spacer separates samples in each section from other samples in neighboring sections. If the marker is not placed correctly, it can block part of the image signal. The offset error can happen across multiple neighboring sections as shown in FIG. 5C. The top portions of nine sections in this figure appear as dark colored. The dark portion on top part of the sections increases as we move from left to right. Space shift issue is an operational error as it is caused by inaccurate placement of marker by laboratory technicians during preparation of samples on image generating chip. FIG. 5D presents three more examples of failed images of sections due to spacer shift failure. A box 525 shows five section images with spacer shift failure as top portions of the section images are dark colored increasing in width from top right to top left. A box 527 shows two section images that indicate failed process due to spacer shift issue at the bottom portions of the sections. Similarly, a box 529 shows images of two sections that failed due to space shift issue.

Figure 5E:
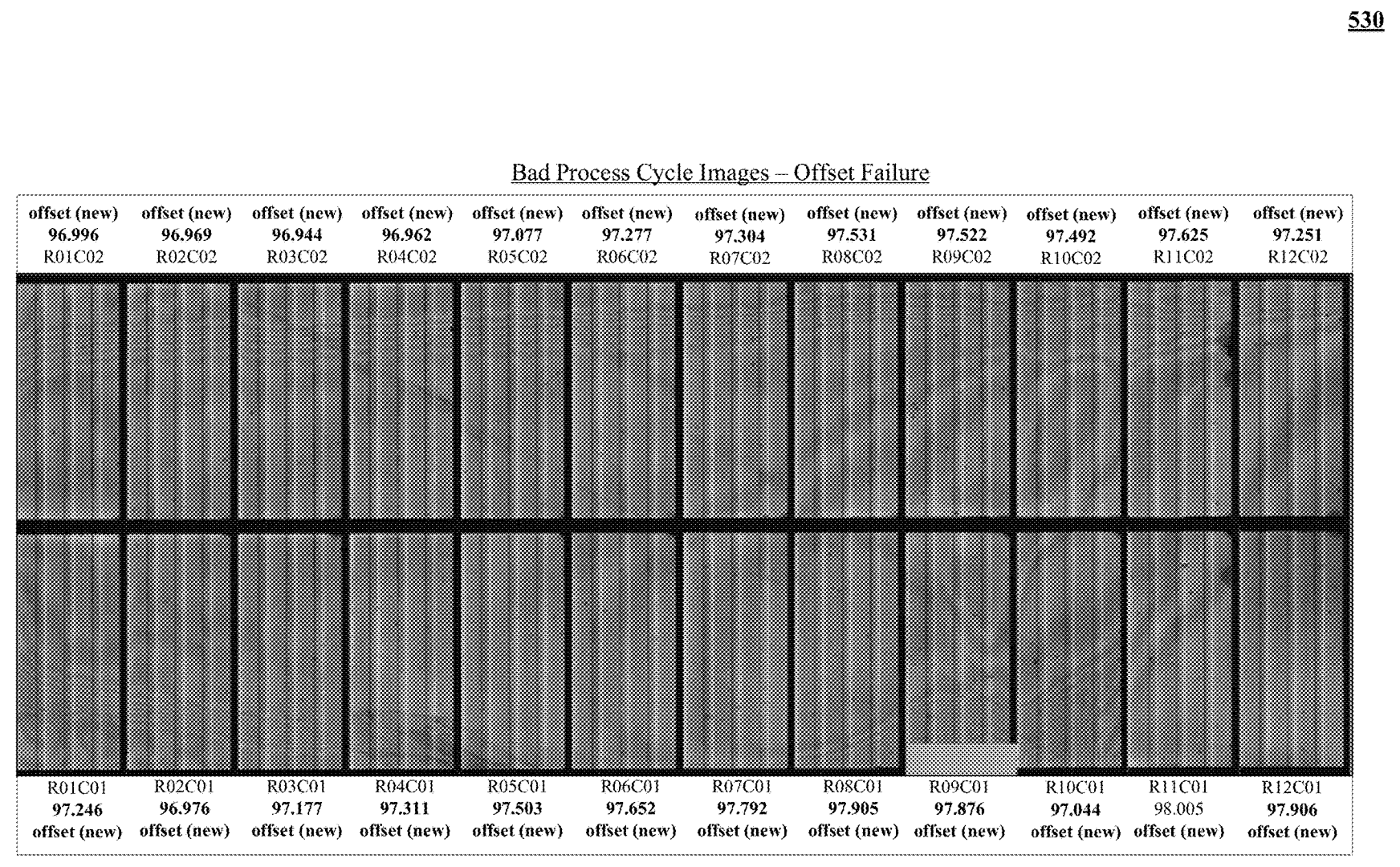

FIG. 5E shows an example of failed images of sections due to unsuccessful processing caused by offset failure. In offset failure, images of sections on the image generating chip are shifted to one side. For example, in the illustration 530, all section images on the image generating chip are shifted towards left side thus the dark colored outer border of the image generating chip on the left edge is cutoff from the image. Offset failures can be caused by scanning errors such as scanner misalignment or misplacement of image generating chip on the chip carrier.

Figure 5F:
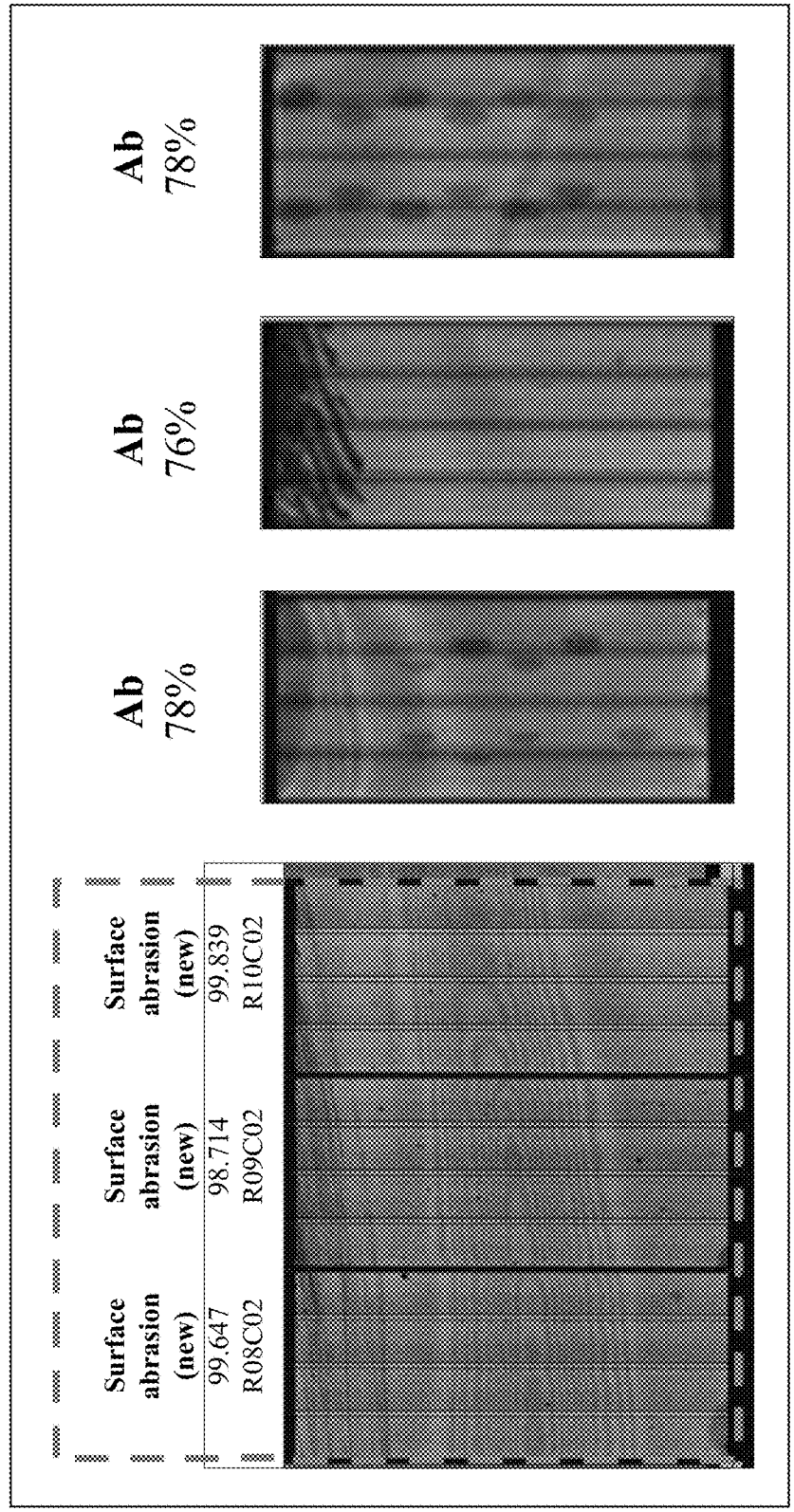
FIG. 5F presents examples of failed section images due to surface abrasion failure.

FIG. 5F shows examples of failed section images due to surface abrasion failure. The surface abrasion is caused by scratches on surface of sections in image generating chip during manufacturing process or during preparation of samples on sections. The scratches are visible as lines on images of the sections as shown in illustration 535. Note that despite call rate values are above pass threshold for three sections in a broken line box on the left, the images are labeled as failed due to surface abrasion failure.

Figure 5G:
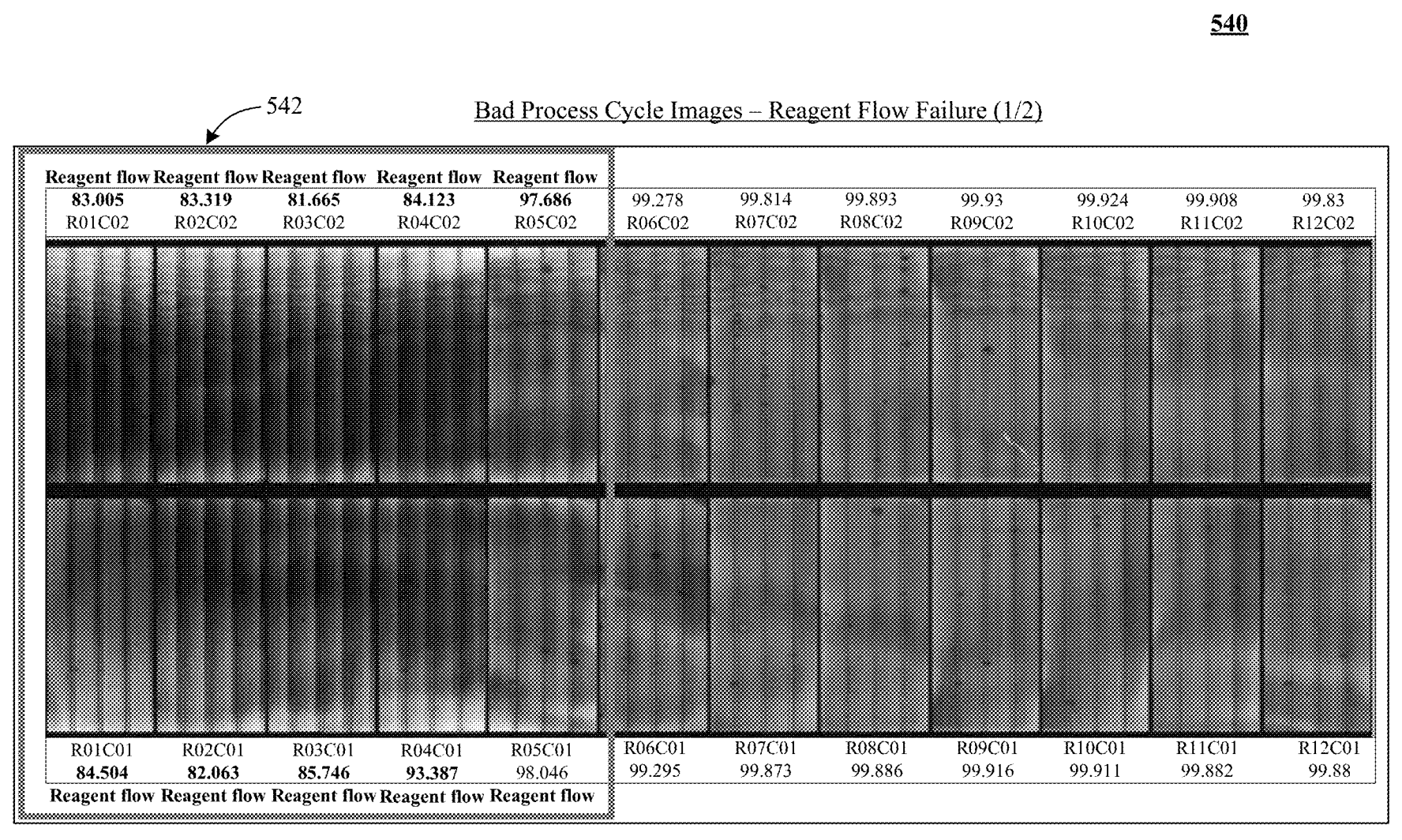
Figure 5H:
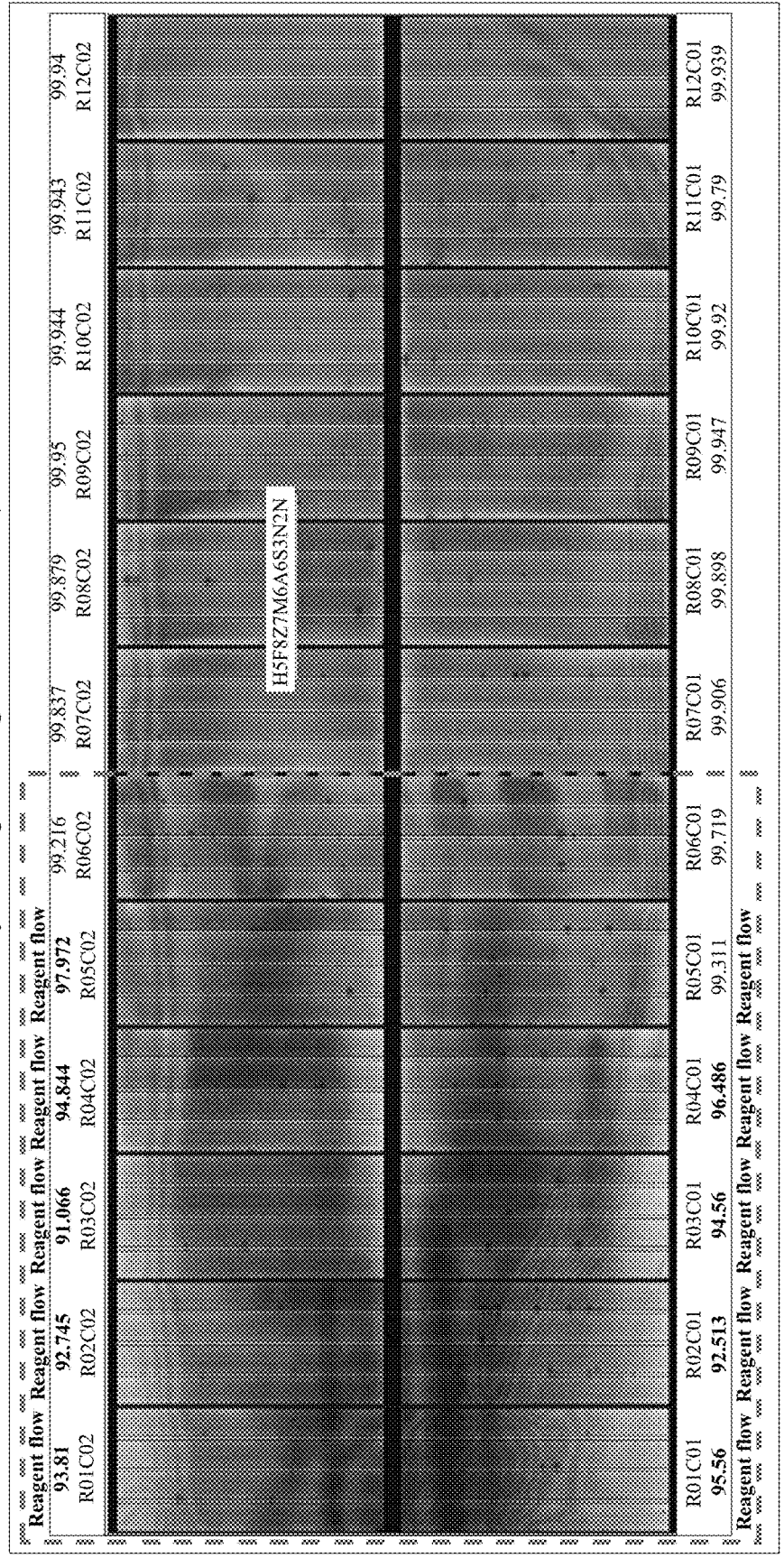

FIG. 5G is an illustration 540 of failed section images due to reagent flow failure. Ten section images in a box 542 are labeled as failed images due to reagent flow failure. The section images failed due to unsuccessful process caused by improper reagent flow. During genotyping process, reagent is introduced in image generating chip from one side. The reagent flows from one end of the image generating chip towards the opposite end and completely covers all sections. Sometimes, there is an issue in flow of the reagent, and it does not propagate evenly to all sections. In this case, the reagent may become dry when sufficient amount of reagent does not cover a section. Improper reagent flow can reduce the strength of emitted signal from some sections as the fluorescence dye may not be evenly distributed over all sections thus impacting the image quality. The failed images due to reagent flow failure can appear as darker in color compared to section images representing successful process cycle. FIG. 5H shows further examples of failed section images due to reagent flow failure in an illustration 545. The reagent flow failure can impact multiple neighboring sections in a region of the image generating chip as shown in FIG. 5G and FIG. 5H.

Figure 5I:
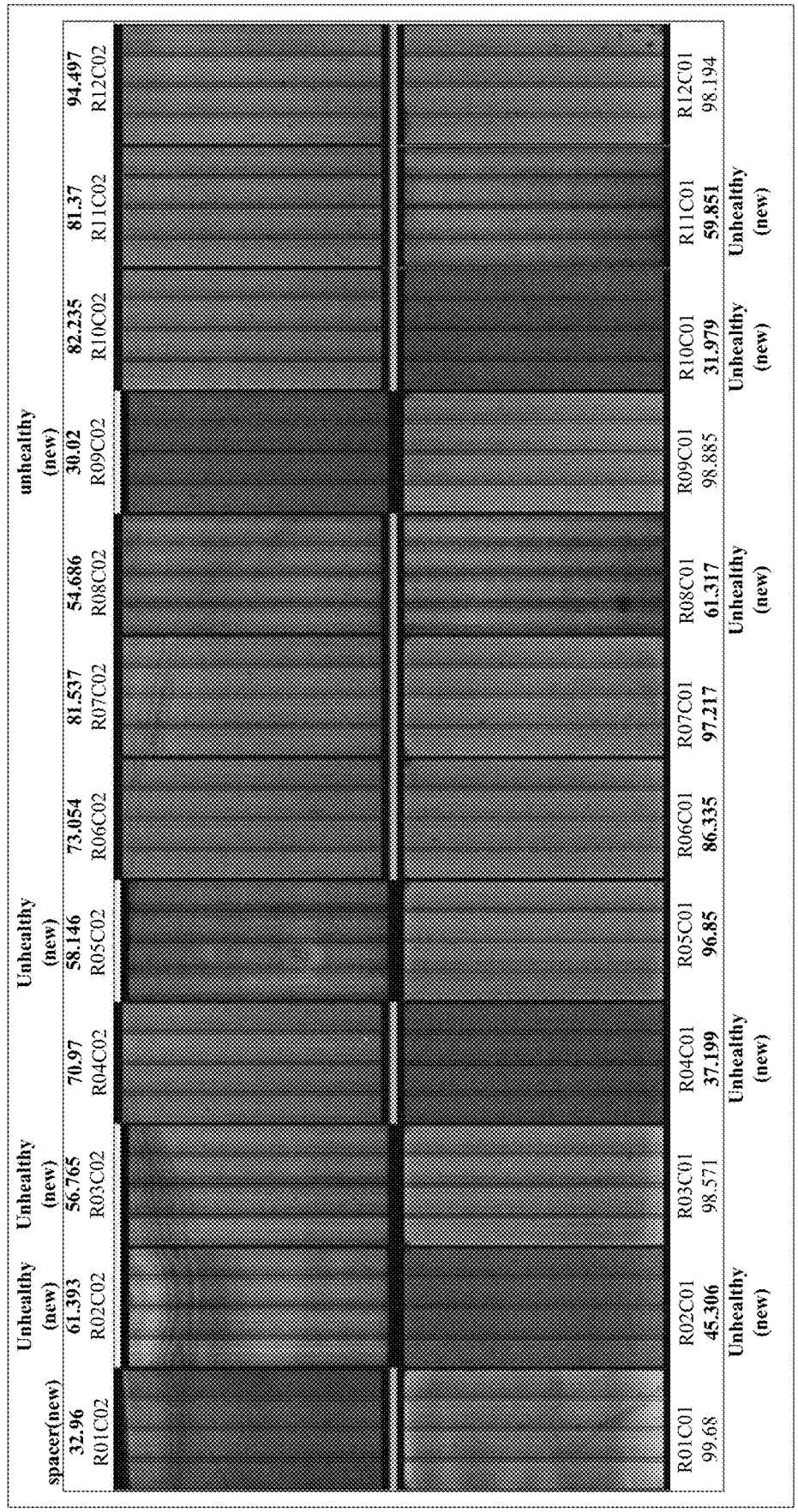
FIG. 5I presents examples of failed or unhealthy section images for which source of failure is unknown.

FIG. 5I presents examples of failed images due to unknown reasons. The failed section images are labeled as "unhealthy". The failed images in unhealthy class of failures can be due to mixed or unidentified causes and weak signals. The illustration 550 of the images of sections also show an example of spacer failure for section on the top left of the image generating chip. The image section on the top left position (row 1 and column 2) is labeled as spacer failure. It can be seen that top portion of the failed section image is dark colored. The portion of dark colored region on the top increases from right corner of the section image to the left corner.

Principal Component Analysis-Based Feature Generation

Figure 6A:
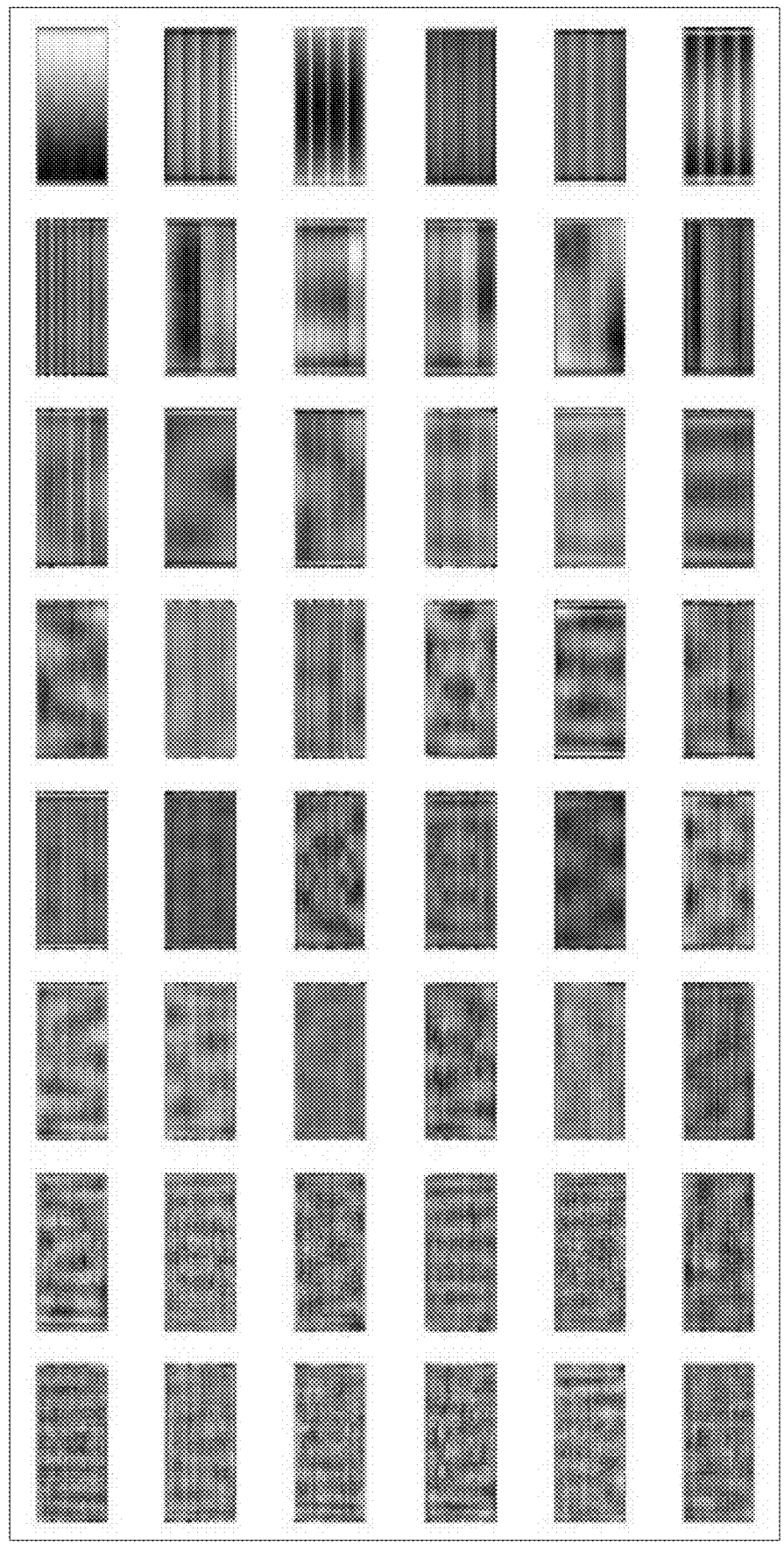
FIGS. 6A and 6B are examples of basis of 96 Eigen image components selected by rank ordering principal components generated using Principal Component Analysis (PCA).
Figure 6B:
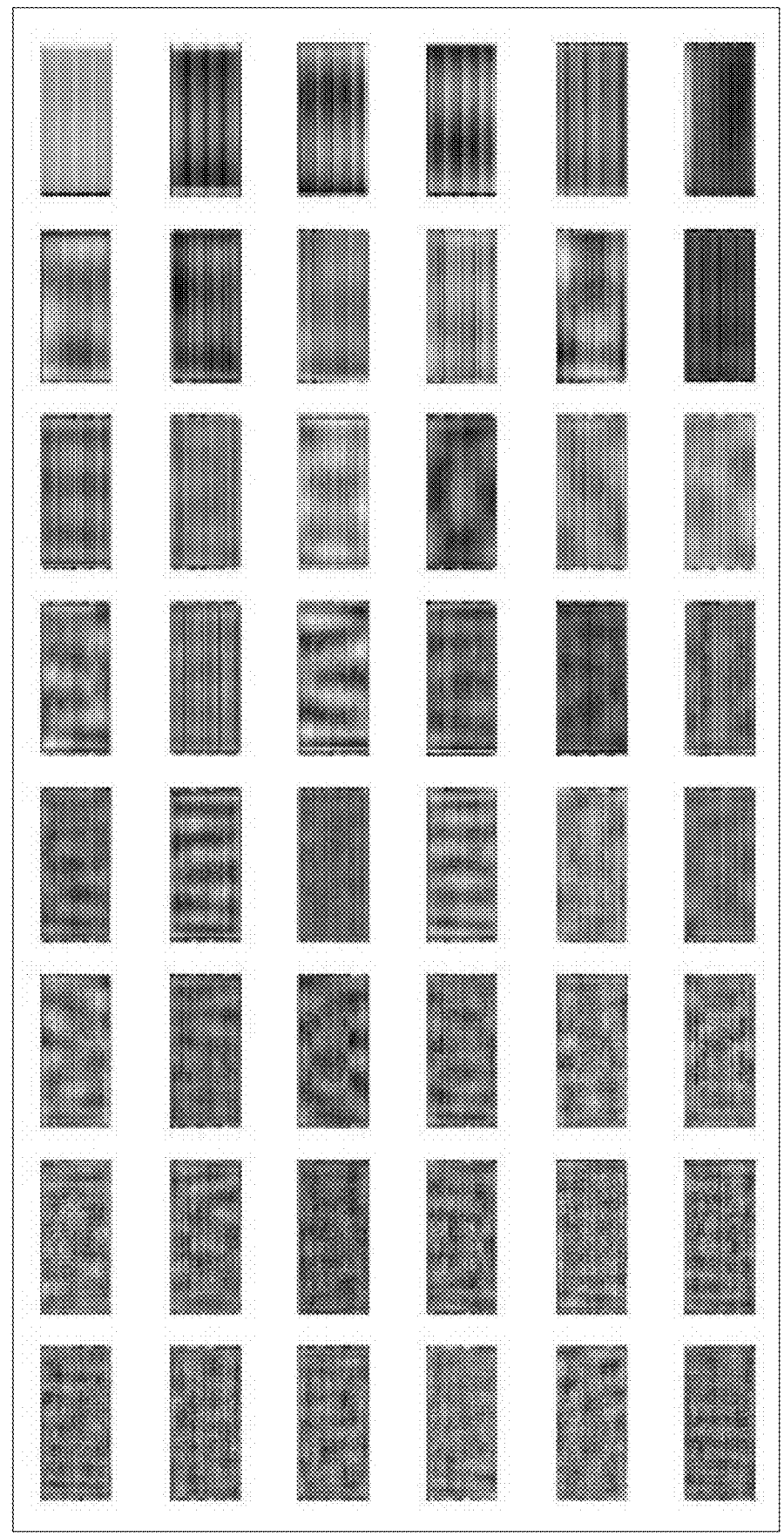
Figure 6C:
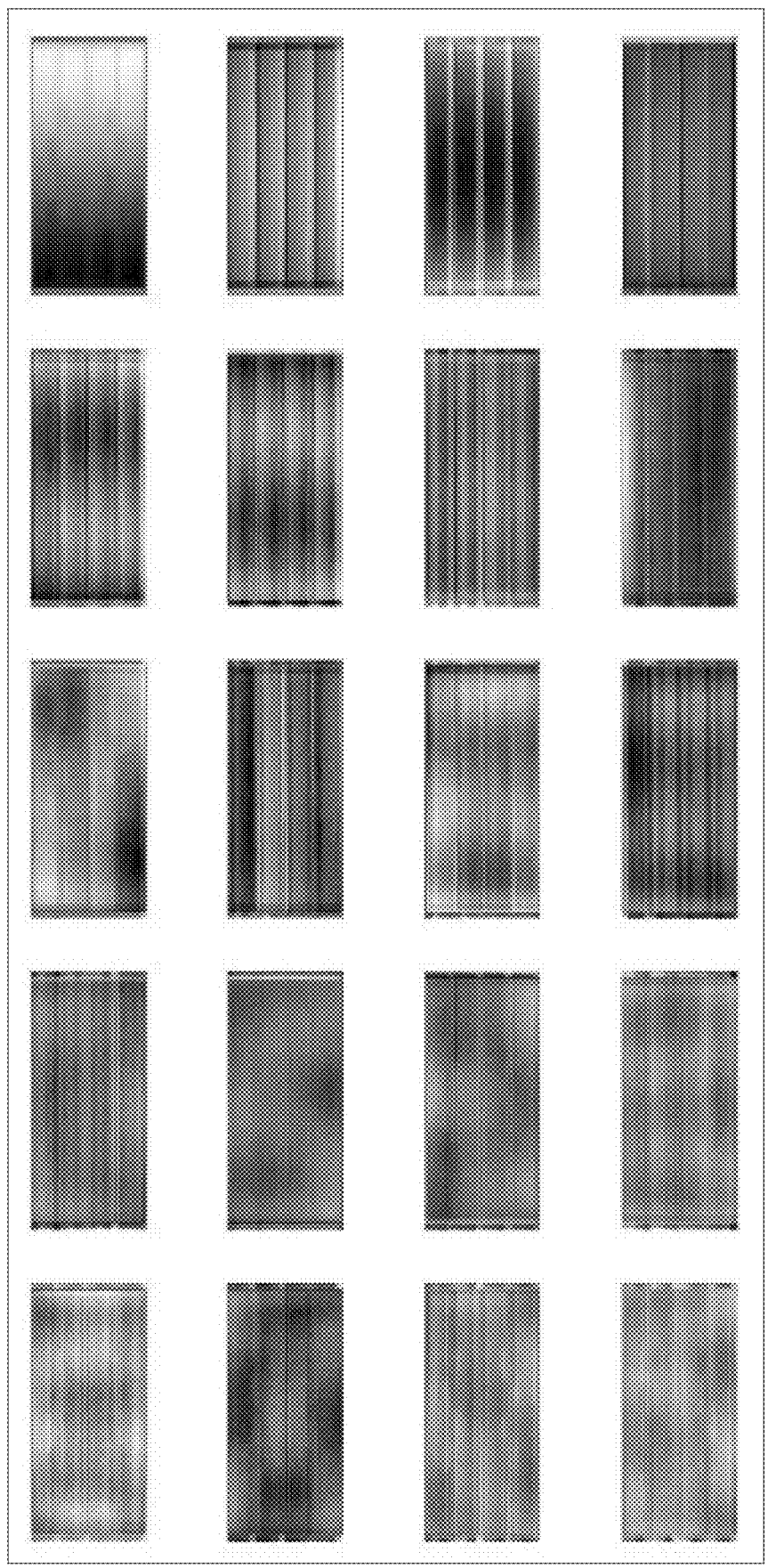
FIGS. 6C and 6D are an enlargement of the top 40 Eigen image components selected from the 96 images in FIG. 6A and FIG. 6B.
Figure 6D:
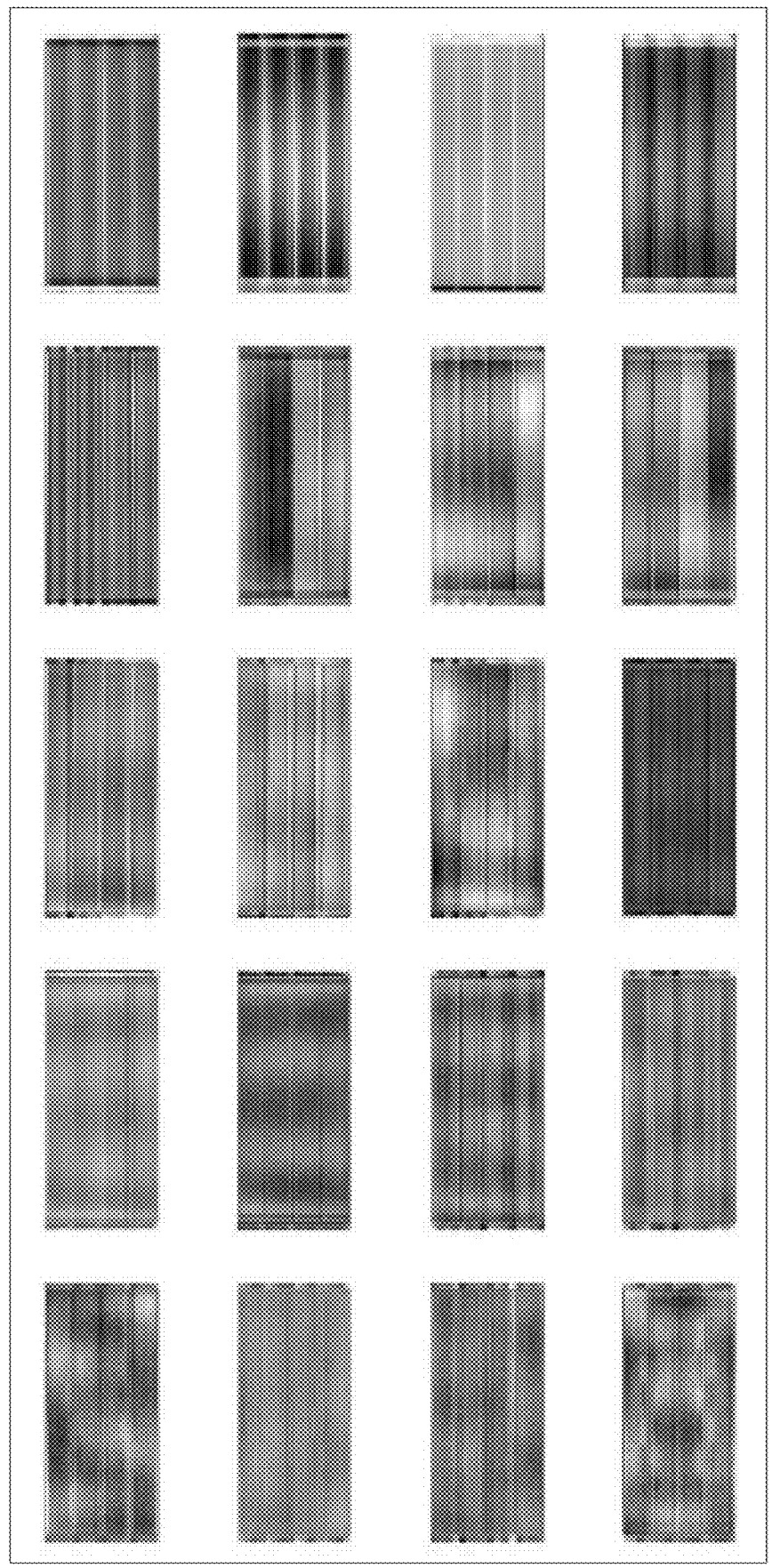

We now present examples of Eigen images, which, in the field of facial recognition, are referred to as Eigen faces. From tens of thousands of labeled images, a linear basis of 40 to 100 or more image components is identified. FIG. 6A and FIG. 6B present an example of 96 Eigen images (610 and 611) obtained by applying Principal Component Analysis (PCA). The 96 Eigen images are selected based on rank ordering of components according to a measure of explained variability as presented above. FIG. 6C and FIG. 6D show top 40 ranked Eigen images (620 and 621) from the 96 Eigen images in FIG. 6A and FIG. 6B. In one implementation, it was observed that 40 components explained most of the variability. Additional components selected appeared to reflect patterns of noise or natural variability in sample processing.

Figure 7A:
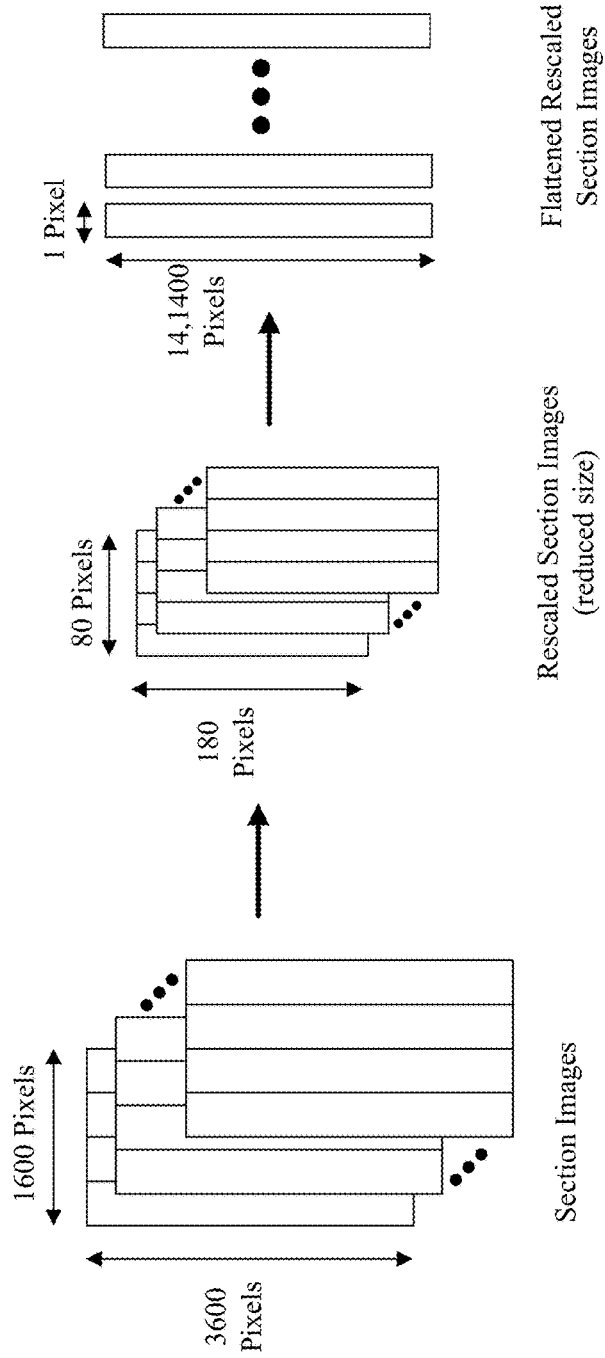
FIG. 7A illustrates image rescaling and flattening of section images for input to Principal Component Analysis.
Figure 7B:
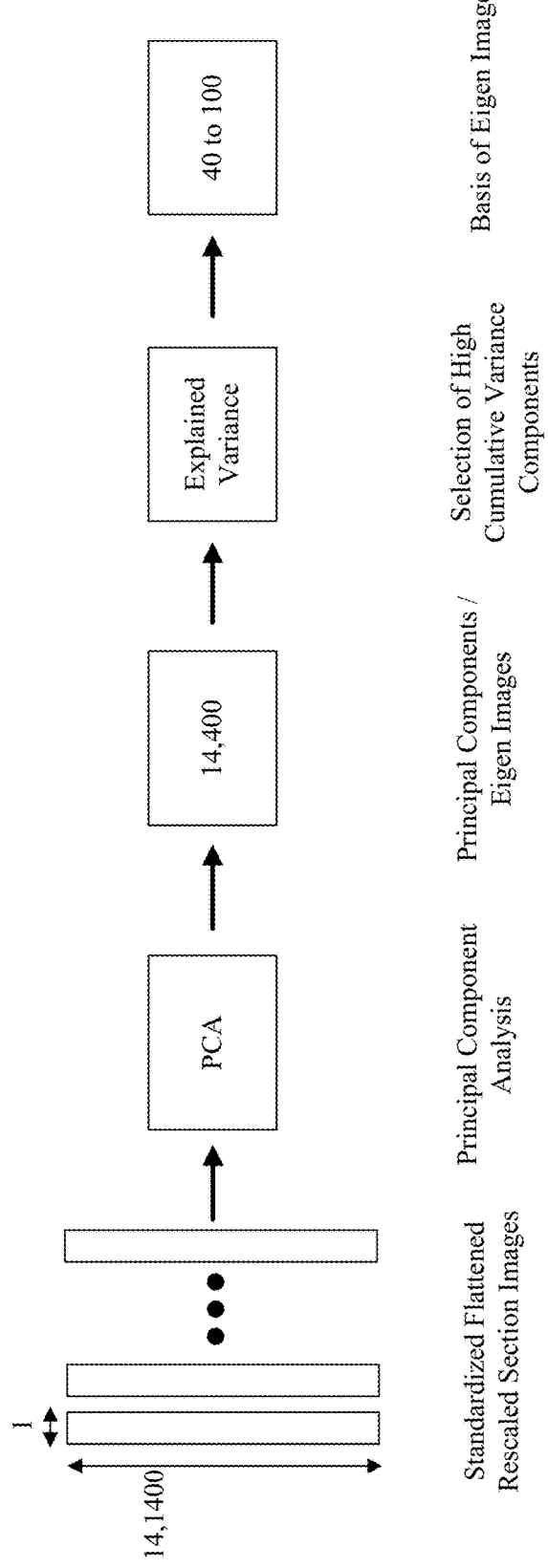
FIG. 7B illustrates creation of a basis of Eigen images using Principal Component Analysis.

We now describe dimensionality reduction and creation of basis of Eigen images using PCA. The first step is to reduce the resolution of images of sections and prepare the reduced images for input to PCA. FIG. 7A (labeled 710) shows section images of 3600×1600 pixels resolution that are rescaled 20 times resulting in reduced section images of size 180×80 pixels. The rescaled section images are flattened. The resulting flattened rescaled section images is a one-dimensional array, i.e., 14,400×1 pixels each. The flattened rescaled section images are standardized as explained above, thus resulting in standardized flattened rescaled section images as shown in FIG. 7B (labeled 740) which are given as input to PCA. The PCA thus produces 14,400 principal components or Eigen images. Each input image is a vector in 14,400-dimensional space. We then use explained variance to rank order principal components or Eigen images and create a basis, for instance a basis of 40 to 100 components. The components form a basis of a linear space.

Image Segmentation-Based Feature Generation

Figure 8A:
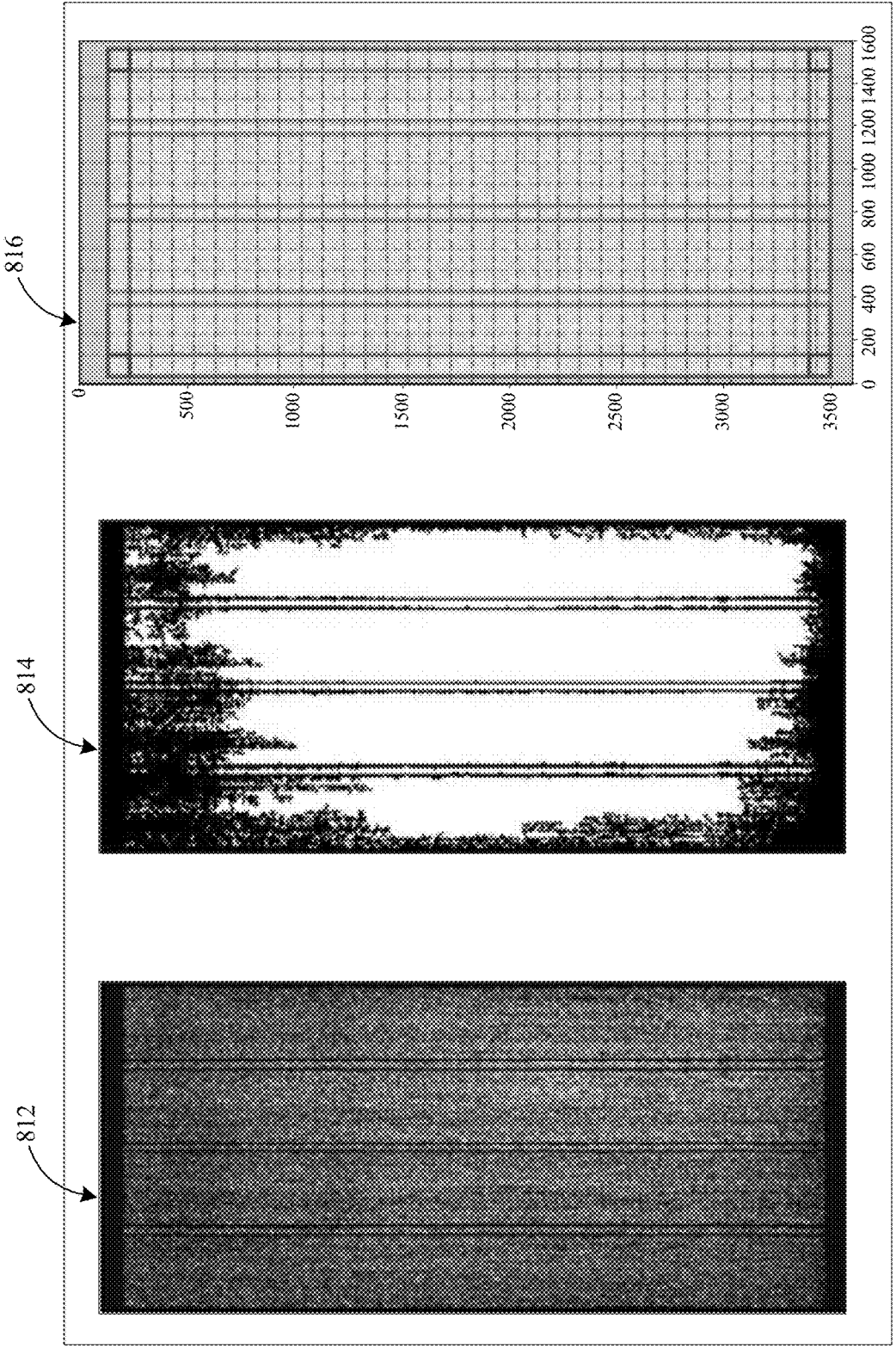
FIG. 8A illustrates an example of feature generation using intensities of areas of sections.

The second image processing technique to generate features from images of section involves thresholding of image areas or segments. FIG. 8A shows an example 810 of segmentation-based feature generation applied to a section image. The illustration 812 is a production image of a section of an image generating chip. We apply image transformation to transform this grayscale production image 812 to generate a counterpart binary image 814. In one implementation, some or all of the five steps presented above with reference to image transformer 257 can be performed to transform the grayscale image to a binary image. The black pixels in binary image 814 indicate unhealthy or bad image pixels while bright pixels indicate healthy or good image pixels.

The illustration 816 on the right is an example schematic of a section indicating various areas of the section and borders or lines around these areas. The areas from which intensity of the fluorescent signal is recorded are also referred to as active areas or regions of interest. For example, the section schematic 816 indicates active areas of four slots that run parallel to each other from top to bottom. The areas of the section image that are not active areas are filtered out of the image. For examples, the boundary areas of slots that are separated from each other by vertical lines that indicate boundaries or borders of slots. Similarly, the borders on the four sides of the section image can be filtered out. The segmentation technique can divide the section images into 4 to 20 or more segments or active areas. The thresholding determines how much of an active area is producing a desired signal strength.

The number of active areas determine the number of features generated per image. For example, if the section image is segmented into eight active areas, then image intensity from eight active areas of the transformed image and the image intensity values from the same eight active areas of the original section image before transformation are given as input to the classifier. Thus, in this example, a total of 16 features per section image will be given to the classifier. An average intensity of the signal strength from an active area can be used as input to a classifier. For example, if the section image is segmented into eight active areas then average intensity of these eight active areas is calculated for both grayscale image and binary image. These sixteen intensity values are given as input to the classifier to classify the section image as good vs bad. Other segmentation schemes can be used which divide the image into fewer or more segments such as 4, 12, 17 or more segments per image. If given as input to a random forest classifier, a subset of features is randomly selected for each decision tree. The decision tree votes the image as healthy or unhealthy. The majority votes in random forest are used to classify the image. In one implementation, the value of number of trees in the random forest classifier is in the range of 200 to 500 and the value of the depth of the model is in the range of 5 to 40. The patterns of failures among areas and sections of an image generating chip can be further evaluated for root cause classification.

Figure 8B:
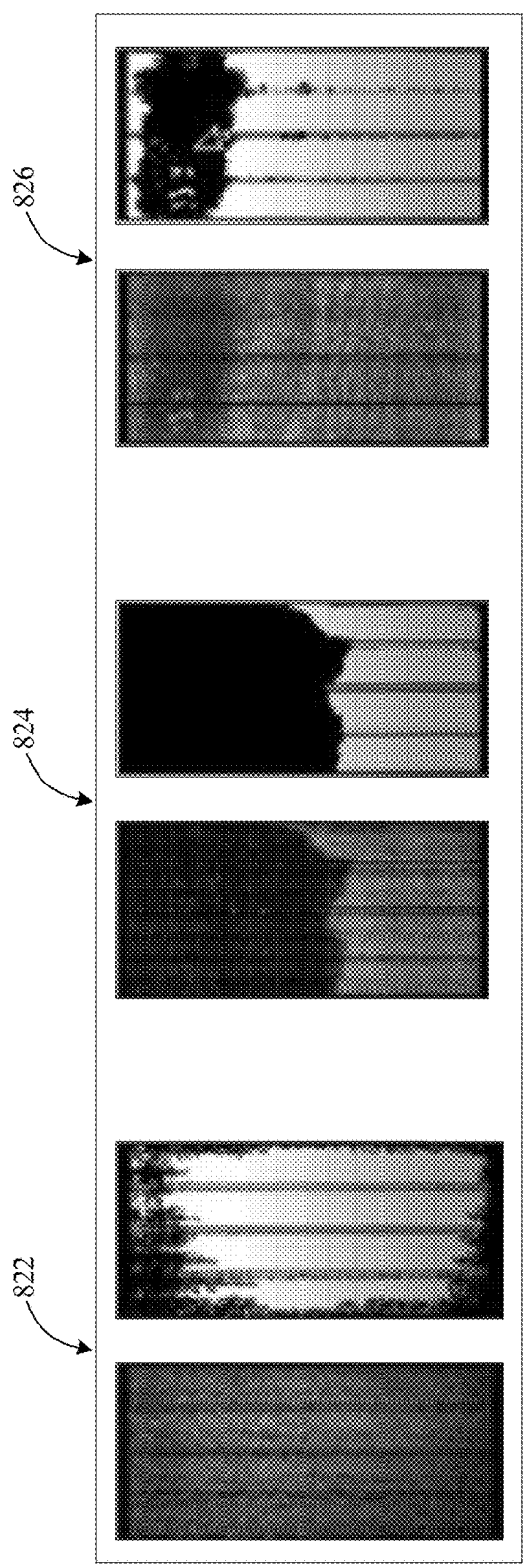
FIG. 8B illustrates another example of feature generation using intensities of areas of sections.

FIG. 8B presents an illustration 820 of three pairs of section images 822, 824, and 826. The left image in each pair is the pre-transformed grayscale section image and the right image in each pair is processed binary image after applying the image transformations as described with reference to FIG. 2. The first image pair 822 is a production image of a successful genotyping process. The second image pair 824 is a production image of failed production image due to hybridization (or hyb) failure. The third image pair 826 is of a failed image due to surface abrasion issue.

One Vs. the Rest (OvR) Classification

Figure 9:
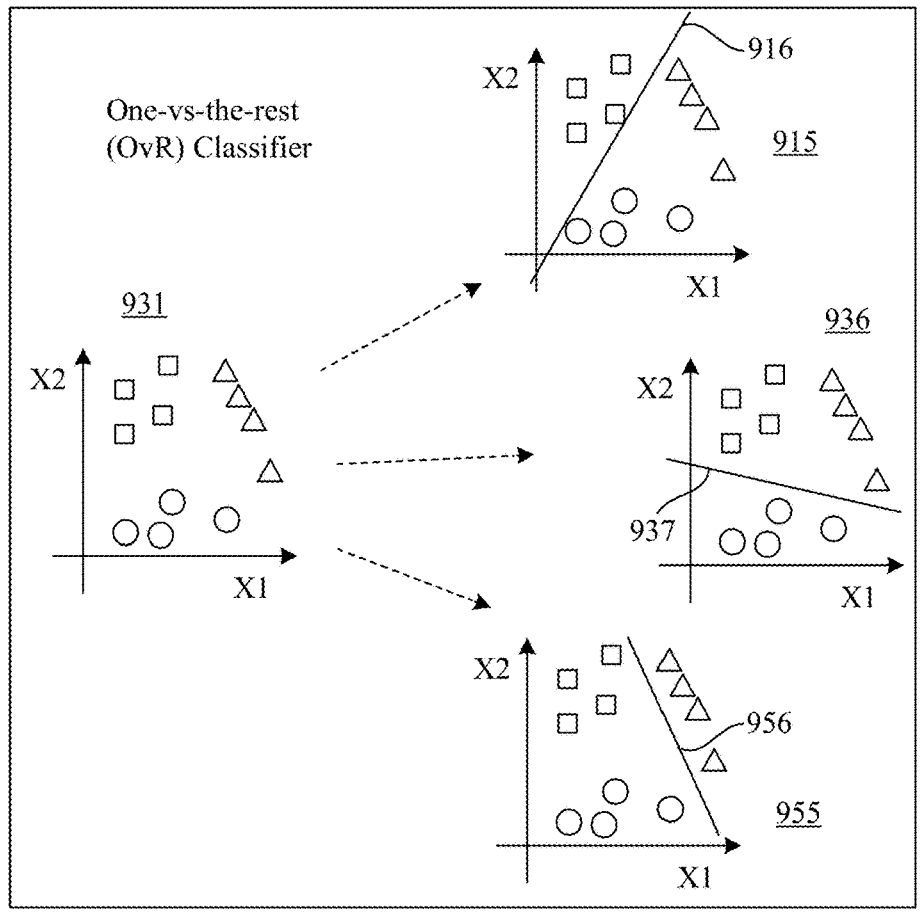
FIG. 9 is a graphical illustration of one-vs-the-rest (OvR) classifier.

FIG. 9 presents graphical illustrations 900 of running one-vs-the-rest classifier. The graphs show examples of running one-vs-the-rest (OvR) classifier on a data set consisting of samples belonging to three classes (squares, circles, and triangles) as shown in the left graph 931. A first hyperplane 916 as shown in the top right graph 915 shows a hyperplane determination for the square class as the ground truth. The hyperplane 916 partitions the data points in the square class from the rest of the data points (circles and triangles). Similarly, graphs 936 and 955 respectively partition data points in circle and triangle classes from other classes in the data via hyperplanes 937 and 956 respectively. The position of the hyperplane is determined by the weight vector. The training algorithm attempts to maximize the margin of the hyperplane from the ground truth class for generalization, however it may result in incorrect classification of one or more data points. We apply OvR classification to distinguish section images from process cycles belonging to a good class from images belonging to multiple bad classes.

Random Forest Classifiers

The technology disclosed can apply a variety of classifiers to distinguish images from good or healthy images from bad or unhealthy images belonging to multiple failure classes. Classifiers applied includes random forest, K-nearest neighbors, multinomial logistic regression, and support vector machines. We present the implementation of the technology disclosed using random forest classifier as an example.

Random forest classifier (also referred to as random decision forest) is an ensemble machine learning technique. Ensembled techniques or algorithms combine more than one technique of the same or different kind for classifying objects. The random forest classifier consists of multiple decision trees that operate as an ensemble. Each individual decision tree in random forest acts as base classifier and outputs a class prediction. The class with the most votes becomes the random forest model's prediction. The fundamental concept behind random forests is that a large number of relatively uncorrelated models (decision trees) operating as a committee will outperform any of the individual constituent models.

The technology disclosed applies the random forest classifiers in a two-staged classification process. A first trained random forest classifier performs the task of separating successful production images from unsuccessful production images. A second trained random forest classifier performs the task of root cause analysis of unsuccessful production images by predicting the failure class of an unsuccessful image. This two-stage classification was selected due to dominance of successful production runs but a one-stage classification can also be used. Another reason for selecting the two-stage approach is that it allows us to control the sensitivity threshold for classifying an image as a healthy or successful production image versus an unhealthy or a failed production image. We can increase the threshold in first stage classification thus causing the classifier to classify more production images as failed images. These failed images are then processed by the second stage classifier for root cause analysis by identifying the failure class.

Training of Random Forest Classifiers

Figure 10A:
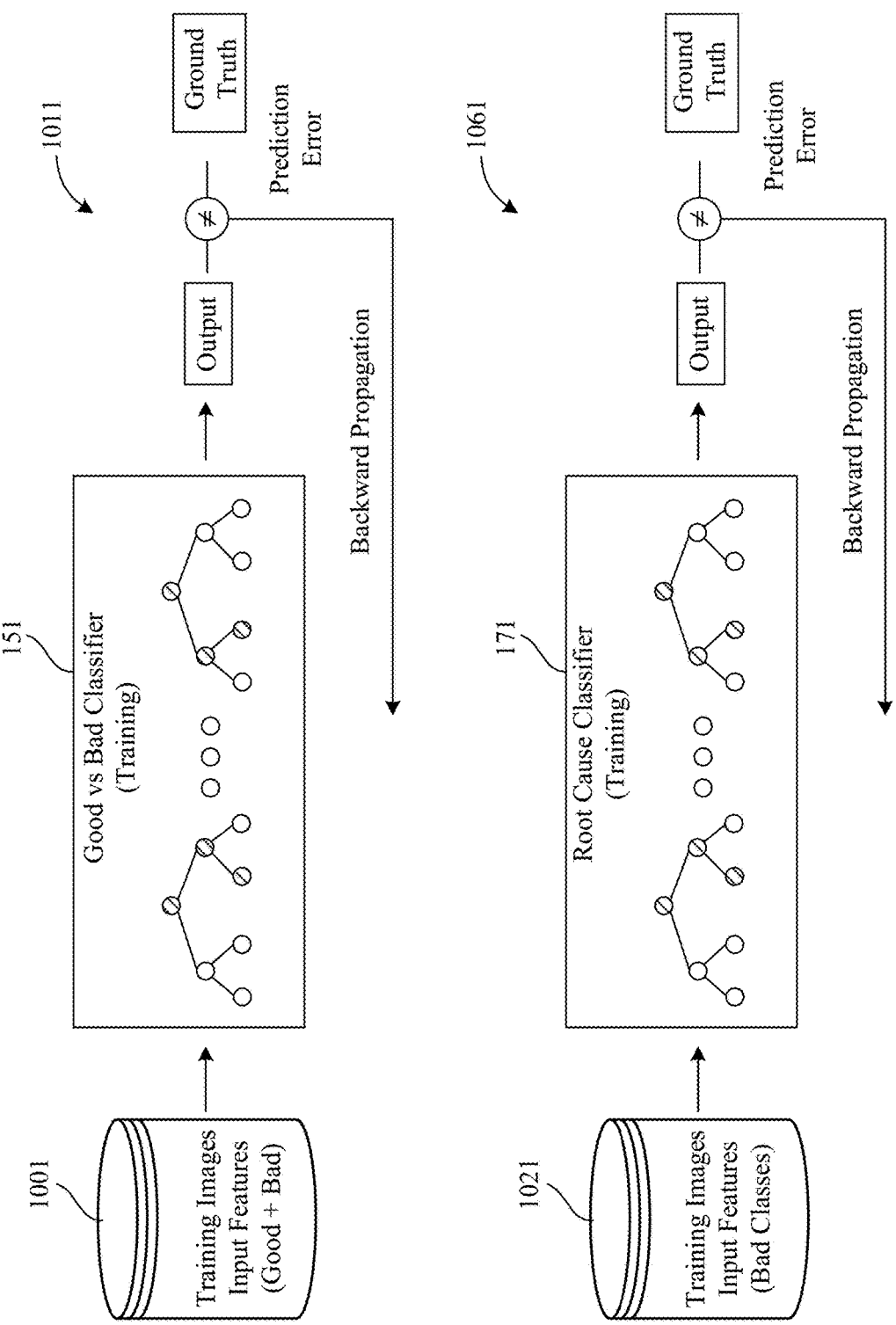
FIG. 10A illustrates training of a binary (good vs. bad) classifier and a multiclass (root cause) classifier using labeled training data comprising process cycle images.

FIG. 10A describes training of two random forest classifiers as shown in an illustration 1000. The training data comprises of input features for the labeled process cycle images stored in the training database 138 as shown in FIG. 1. In one example training of the classifiers, we used 20,000 labeled production images of sections. The labeled images include both good images from successful production cycles and failed images from unsuccessful production cycles. The size of the training database 138 will grow as more labeled production images are received from laboratories performing the genotyping process.

In one implementation, we used 96 weights of components of labeled production images to train random forest classifiers. A random forest classifier with 200 decision trees and a depth of 20 worked well. It is understood that random forest classifiers with a range of 200 to 500 decision trees and a range of depth from 10 to 40 is expected to provide good results for this implementation. We tuned the hyperparameters using randomized search cross-validation. The search range for depth was from 5 to 150 and search range for number of trees was from 100 to 500. Increasing the number of trees can increase the performance of the model however, it can also increase the time required for training. A training database 1001 including features for 20,000 production cycle images is used to train the binary classifier which is labeled as Good vs Bad classifier 151. The same training database can be used to training root cause classifier 171 to predict the failure class. The root cause classifier 171 is trained on training database 1021 consisting of only the bad or failed production images as shown in FIG. 10A.

Decision trees are prone to overfitting. To overcome this issue, bagging technique is used to train the decision trees in random forest. Bagging is a combination of bootstrap and aggregation techniques. In bootstrap, during training, we take a sample of rows from our training database and use it to train each decision tree in the random forest. For example, a subset of features for the selected rows can be used in training of decision tree 1. Therefore, the training data for decision tree 1 can be referred to as row sample 1 with column sample 1 or RS1+CS1. The columns or features can be selected randomly. The decision tree 2 and subsequent decision trees in the random forest are trained in a similar manner by using a subset of the training data. Note that the training data for decision trees is generated with replacement i.e., same row data can be used in training of multiple decision trees.

The second part of bagging technique is the aggregation part which is applied during production. Each decision tree outputs a classification for each class. In case of binary classification, it can be 1 or 0. The output of the random forest is the aggregation of outputs of decision trees in the random forest with a majority vote selected as the output of the random forest. By using votes from multiple decision trees, a random forest reduces high variance in results of decision trees, thus resulting in good prediction results. By using row and column sampling to train individual decision trees, each decision tree becomes an expert with respect to training records with selected features.

During training, the output of the random forest is compared with ground truth labels and a prediction error is calculated. During backward propagation, the weights of the 96 components (or the Eigen images) are adjusted so that the prediction error is reduced. The number of components or Eigen images depends on the number of components selected from output of principal component analysis (PCA) using the explained variance measure. During binary classification, the good vs. bad classifier uses the image description features from the training data and applies one-vs-the-rest (OvR) classification of the good class (or healthy labeled images) versus the multiple bad classes (images labeled with one of the six failure classes). The parameters (such as weights of components) of the trained random forest classifier are stored for use in good vs. bad classification of production cycle images during inference.

The training of the root cause classifier 171 is performed in a similar manner. The training database 1021 comprises of features from labeled process cycle images from bad process cycles belonging to multiple failure classes. The random forest classifier 171 is trained using the image description features for one-vs-the-rest (OvR) classification of each failure class verses the rest of the labeled training examples.

Classification Using Random Forest Classifiers

Figure 10B:
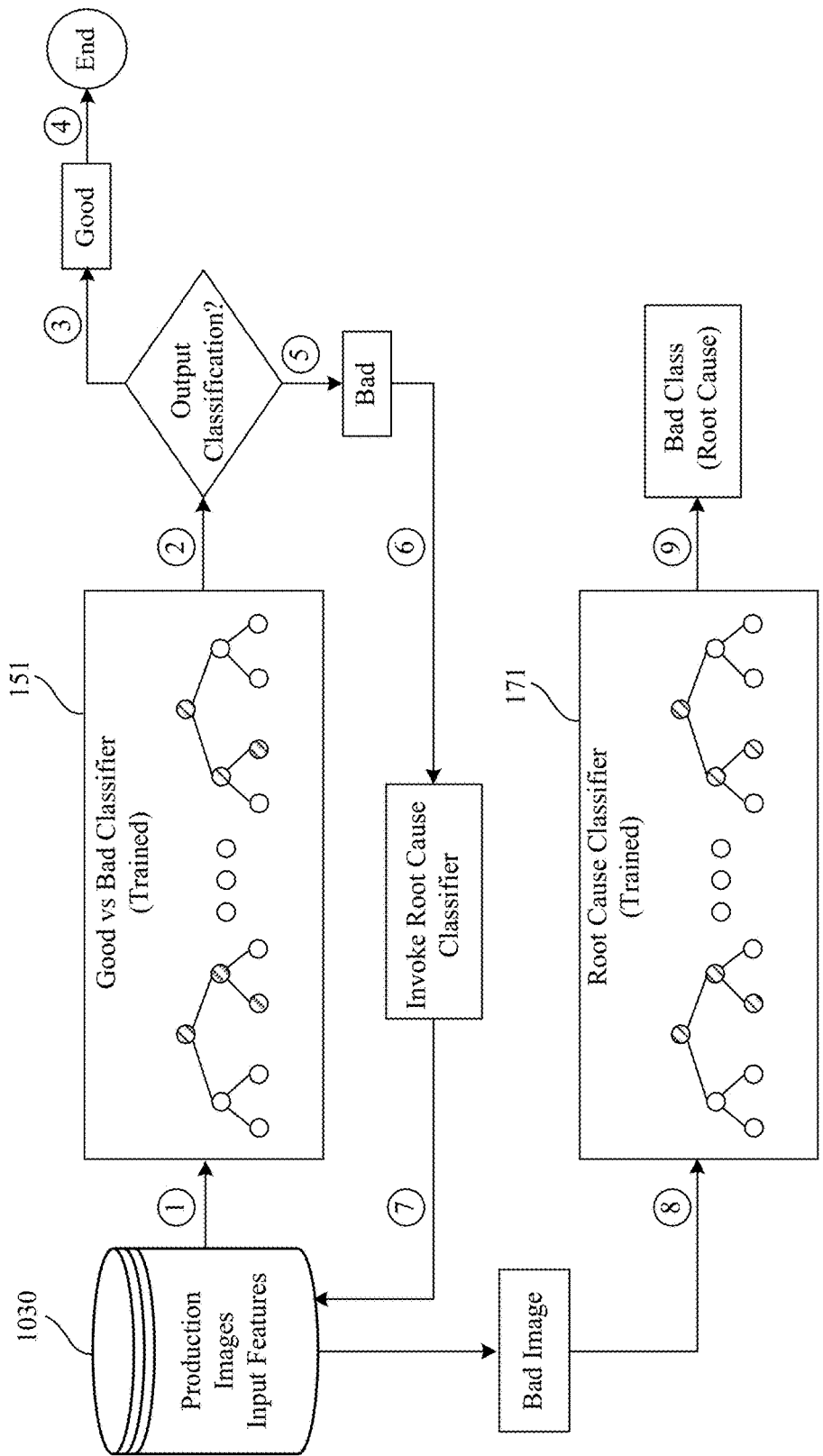
FIG. 10B illustrates two-step process in which production process cycle images are classified as good vs. bad and further a failure category of the bad images is determined.

We now describe the classification of production images using the trained classifiers 151 and 171. FIG. 10B shows the two-stage classification 1080 of production images using the good vs. the bad classifier 151 in a first stage and a root cause classifier 171 in a second stage. The process is presented using a sequence of process flow steps labeled from 1 to 9. The process starts at a step 1 by accessing a trained random forest classifier labeled as good vs. bad classifier 151. Input features of production images stored in a database 1030 are provided as input to the classifier 151. The classifier distinguishes good images belonging to successful process cycle from bad images belonging failed process cycles. The bad images belong to multiple failure classes for example, each image can belong to one of the six failure classes as described above. The trained classifier accesses a basis of Eigen images with which to analyze a production image. The trained classifier creates image description features for the production image based on linear combination of Eigen images. The weights of the Eigen images are learned during the training of the classifier as described above.

As we apply the one-versus-the-rest classification, all decision trees in the random forest classifier predict output for each class, i.e., whether the image belongs to one of the seven classes (one good class and six failure classes). Therefore, each decision tree in the random forest will output seven probability values, i.e., one value per class. The results from the decision trees are aggregated and majority vote is used to predict the image as good or bad. For example, if more than 50% of the decision trees in the random forest classify the image as good, the image is classified as a good image belonging to a successful production cycle. The sensitivity of the classifier can be adjusted for example, by setting the threshold higher will result in more images classified as bad. In process step 2, the output from the classifier 151 is checked. If the image is classified as a good image (step 3), the process ends (step 4). Otherwise, if the image is classified as a bad image indicating a failed process cycle (step 5), the system invokes root cause classifier 171 (step 6).

The root cause classifier is applied in the second stage of the two-stage process to determine the class of failure of the bad image. The process continues in the second stage by accessing the production image input feature for the bad image (step 7) and providing the input features to the trained root cause classifier 171 (step 8). Each decision tree in the root cause classifier 171 votes for the input image features by applying the one-vs-the-rest classification. In this case, the classification determines whether the image belongs to one of the six failure class versus the rest of the five failure classes. Each decision tree provides classification for each class. Majority votes from decision trees determine the failure class of the image (step 9).

We can use other classifiers to classify good section images vs. bad section images and perform root cause analysis. For example, the technology disclosed can apply K-nearest neighbors (k-NN or KNN) algorithm to classify section images. The k-NN algorithm assumes similar examples (or section images in our implementation) exist in close proximity. The k-NN algorithm captures the idea of similarity (also referred to as proximity, or closeness) by calculating the distance between data points or images. A straight-line distance (or Euclidean distance) is commonly used for this purpose. In k-NN classification, the output is a class membership, for example, a good image class or a bad image class. An image is classified by a plurality of votes of its neighbors, with the object being assigned to the class most common among its k nearest neighbors. The value of k is a positive integer.

To select the right value of k for our data, we run the k-NN algorithm several times with different values of k and choose the value of k that reduces the number of errors we encounter while maintaining the algorithm's ability to accurately make predictions when it is given data that it has not seen before. Let us assume, we set the value of k to 1. This can result in incorrect predictions. Consider we have two clusters of data points: good images and bad images. If we have a query example that is surrounded by many good images data points, but it is near to one bad image data point that is also in the cluster of good images data points. With k=1, the k-NN incorrectly predicts that the query example is bad image. As we increase the value of k, the prediction of the k-NN algorithm become more stable due to majority voting (in classification) and averaging (in regression). Thus, the algorithm is more likely to make more accurate predictions, up to a certain value of k. As the value of k is increased, we start observing increasing number of errors. The value of k in the range of 6 to 50 is expected to work.

Examples of other classifiers that can be trained and applied by the technology disclosed include multinomial logistic regression, support vector machines (SVM), gradient boosted trees, Naïve Bayes, etc. We evaluated the performance of classifiers using three criteria: training time, accuracy and interpretability of results. Random forest classifier performed better than other classifiers. We briefly present other classifiers in the following text.

Support vector machines classifier also performed equally well as random forest classifier. An SVM classifier positions a hyperplane between feature vector for the good class vs feature vectors for the multiple bad classes. The technology disclosed can include training a multinomial logistic regression. The multinomial regression model can be trained to predict probabilities of different possible outcomes (multiclass classification). The model is used when the output is categorical. Therefore, the model can be trained to predict whether the image belongs to a good class or one of the multiple bad classes. The performance of the logistic regression classifier was less than the random forest and SVM classifiers. The technology disclosed can include training a gradient boosted model which is an ensemble of prediction models such as decision trees. The model attempts to optimize a cost function over function space by iteratively choosing a function that points in the negative gradient direction. For example, the model can be trained to minimize the mean squared error over the training data set. Gradient boosted model required more training time as compared to other classifiers. The technology disclosed can include training Naïve Bayes classifier that assume that the value of a particular feature is independent of the value of any other feature. A Naïve Bayes classifier considers each of the features to contribute independently to the probability of an example belonging to a class. Naïve Bayes classifier can be trained to classify images in a good class vs. multiple bad classes.

Particular Implementations

The technology disclosed applies image classification for evaluation and root cause analysis of genotyping process. Two tasks are performed by the classifiers: separation of successful and unsuccessful (or failed) production images, then root cause analysis of unsuccessful images. The technology disclosed can be applied to process cycle images from genotyping process instruments. Although the technology disclosed is described to classify images from genotyping process, the classification can be applied to images from other types of processes that produce images of samples positioned on image generating chips during the process or at the end of the process.

We first present classification of successful and unsuccessful production images. In one implementation of the technology disclosed, a method is described for training a random forest classifier for classifying genotyping process cycle images. The method to train the classifier includes accessing labelled training examples for images from process cycles belonging to a successful (or good or healthy) class and multiple failure (or bad or unhealthy) classes. The method can include accessing a basis of Eigen images with which to analyze the images. The method includes creating image description features for each labelled training example based on a linear combination of the Eigen images. The method includes training a random forest classifier using the image description features for one-vs-the-rest determination of the successful class vs the multiple failure classes of the labelled training examples. The method can include training other classifiers for one-vs-the-rest determination of the successful class vs the multiple failure classes of the labelled training examples. For example, the method can include training a support vector machine (SVM) classifier. An SVM classifier positions a hyperplane between feature vector for the successful class vs feature vectors for the rest of the classes (or multiple failure classes in our case). The method can include training a multinomial logistic regression. The multinomial regression model can be trained to predict probabilities of different possible outcomes (multiclass classification). The model is used when the output is categorical. Therefore, the model can be trained to predict whether the image belongs to a successful class or one of the multiple failure classes. The method can include training a gradient boosted model which is an ensemble of prediction models such as decision trees. The model attempts to optimize a cost function over function space by iteratively choosing a function that points in the negative gradient direction. For example, the model can be trained to minimize the mean squared error over the training data set. The method can include training Naïve Bayes classifier that assume that the value of a particular feature is independent of the value of any other feature. A Naïve Bayes classifier considers each of the features to contribute independently to the probability of an example belonging to a class. Naïve Bayes classifier can be trained to classify images in a successful class vs. multiple failure classes. The parameters of the trained classifier are stored for use in production of successful vs failed classifications of process cycle images. Classifying the production images using any of the above described classifiers can detect failed production runs. The classifiers can provide a quick feedback to operators about quality of the genotyping process. The feedback from classifiers can be used to correct upstream processes which can reduce wastage of processing time and valuable samples.

The method of training the classifier for genotyping process cycle images can further include creating the basis of Eigen images with which to analyze the images. The method can include accessing the basis of Eigen images. The basis of Eigen images are ordered according to a measure of variability explained. Top ordered basis of Eigen images that cumulatively explain variability above a threshold are selected for analyzing the process cycle images. The method can include analyzing the process cycle images using the selected basis of Eigen image. The random forest classifier can include 100 to 400 decision trees. The depth of the random forest classifier can be between 10 and 40.

In a production implementation, the method classifies production process cycle images as successful or failed. The method includes accessing a random forest classifier trained to distinguish images from process cycles belonging to a successful class from images belonging to multiple failure classes. The method can include accessing a basis of Eigen images with which to analyze a production image and creating image description features for the production image based on linear combination of the Eigen images. The method applies trained random forest classifier to the image description features for one-vs-the-rest determination of the successful class vs the multiple failure classes. The method includes providing notification on a user interface to repeat the process cycle based on a failed process cycle determination.

We now present root cause analysis of unsuccessful (or failed) images. In one implementation of the technology disclosed, a method is described for training a root cause random forest classifier for process cycle images or genotyping process cycle images. The method to train the classifier includes accessing labelled training examples for images from failed process cycles belonging to multiple failure classes. The method also includes accessing a basis of Eigen images with which to analyze the images and creating image description features for each labelled training example based on a linear combination of the Eigen images. The method includes training a random forest classifier using the image description features for one-vs-the-rest determination of each failure class vs the rest of the labelled training examples. The parameters of the trained random forest classifier are stored for use in production of root cause classifications of process cycle images from failed process cycles.

The method of training the root cause classifier can further include creating the basis of Eigen images with which to analyze the images. The basis of Eigen images are ordered according to a measure of variability explained. Top ordered basis of Eigen images that cumulatively explain variability above a threshold are selected for analyzing the process cycle images. The random forest classifier can include 100 to 400 decision trees. The depth of the random forest classifier can be between 10 and 40.

In a production implementation, the method of root cause analysis from a failed process cycle image includes accessing a basis of Eigen images with which to analyze a failed production image and creating image description features for the failed production image based on a linear combination of the Eigen images. The method includes accessing a random forest classifier trained to distinguish images from process cycles belonging to one of the multiple failure classes. The method includes applying the random forest classifier to the image description features for one-vs-the-rest determination among the multiple failure classes, including scoring each of the multiple failure classes vs the rest and using resulting scores to select among the multiple failure classes as a likely root cause of the bad process cycle.

The technology disclosed can use other feature generation and dimensionality reduction techniques to generate input for classifiers. Examples of such techniques include non-negative matrix factorization (NMF), independent component analysis, dictionary learning, sparse principal component analysis, factor analysis, mini-batch K-means. Variations of image decomposition and dimensionality reduction techniques can be used. The technology disclosed can also apply classifiers other than random forest classifiers to classify the process cycles images. Classifiers applied can include random forest, K-nearest neighbors (KNN), multinomial logistic regression, support vector machines (SVM), gradient boosted trees, Naïve Bayes, etc. As larger bodies of labeled images become available, convolutional neural networks such as ImageNet could also be used.

In one implementation, a single method can implement the successful vs failure classifier and the root cause classifier in an end-to-end manner. The input images are given as input to the first classifier that separates successful images from failed images. The method includes accessing a second random forest classifier upon determination that the image description features do not belong to the successful class. The second random forest classifier is trained to distinguish images from process cycles belonging to one of the multiple failure classes. The method includes applying the second random forest classifier to the image description features for one-vs-the-rest determination among the multiple failure classes. The method also includes scoring each of the multiple failure classes vs the rest and using resulting scores to select among the multiple failure classes as a likely root cause of the bad process cycle.

Another implementation of the technology disclosed uses thresholding of areas of images of sections for classifying process cycle images. The method includes determining and applying a threshold, from intensities of pixels in a grayscale production cycle image, with which to classify image pixels into bright and dark classes, transforming the grayscale image into a binary image. The method can include producing the bright and dark image pixel classifications. The method includes segmenting the grayscale image and the transformed binary image into eight or more areas that separate systematic expected noise in the image from signal. The method includes calculating average intensity values for the areas in the grayscale image and the transformed binary image. The method includes accessing a random forest classifier trained to classify the images from process cycles, based on the average intensity values for the areas in the grayscale and the binary images. The images are classified as belonging to a successful class or to a failure class and a confidence score is generated for the classification. The method can include comparing the confidence score generated by the trained random forest classifier to a threshold and classifying the image as successful or failed.

In one implementation, the method presented above further includes, applying a bilateral filter to preserve edges in the production cycle image before transforming the production cycle image.

In one implementation, the method further includes, applying Gaussian blur filter to remove speckle-like noise from the binary image after transforming the production cycle image.

In one implementation, the method further includes, applying morphology operations to fill holes in the binary image after transforming the production cycle image, wherein the morphology operations include erosion and dilation.

The computer implemented methods described above can be practiced in a system that includes computer hardware. The computer implemented system can practice one or more of the methods described above. The computer implemented system can incorporate any of the features of methods described immediately above or throughout this application that apply to the method implemented by the system. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

As an article of manufacture, rather than a method, a non-transitory computer readable medium (CRM) can be loaded with program instructions executable by a processor. The program instructions when executed, implement one or more of the computer-implemented methods described above. Alternatively, the program instructions can be loaded on a non-transitory CRM and, when combined with appropriate hardware, become a component of one or more of the computer-implemented systems that practice the methods disclosed.

Each of the features discussed in this particular implementation section for the method implementation apply equally to CRM and system implementations. As indicated above, all the method features are not repeated here, in the interest of conciseness, and should be considered repeated by reference.

Clauses

1. A method of training a random forest classifier for genotyping process cycle images, including:
accessing labelled training examples for images from process cycles belonging to a successful class and multiple failure classes;
creating image description features for each labelled training example based on a linear combination of Eigen images;
training the random forest classifier using the image description features of the labelled training examples; and
storing parameters of the trained random forest classifier.
2. The method of clause 1, further including:
accessing a basis of Eigen images;
ordering the basis of Eigen images according to a measure of variability explained; and
selecting the top ordered basis of Eigen images that cumulatively explain variability above a threshold; and
analyzing the process cycle images using the selected basis of Eigen images.
3. The method of clause 1, further including training the random forest classifier using the image description features for one-vs-the-rest determination of the successful class vs the multiple failure classes.
4. The method of clause 1, wherein the random forest classifier includes 100 to 400 decision trees.
5. The method of clause 1, wherein the random forest classifier has a depth of 10 to 40.
6. A method of classifying genotyping process cycle images, including:
accessing a random forest classifier trained to distinguish images from process cycles belonging to a successful class from images belonging to multiple failure classes;
creating image description features for production image based on linear combination of Eigen images;
applying the random forest classifier to the image description features; and
providing notification on a user interface to repeat process cycle based on a failed process cycle determination.
7. The method of clause 6, further including training the random forest classifier using the image description features for one-vs-the-rest determination of the successful class vs the multiple failure classes.
8. A method of training a root cause random forest classifier for genotyping process cycle images, including:
accessing labelled training examples for images from failed process cycles belonging to multiple failure classes;
creating image description features for each labelled training example based on a linear combination of Eigen images; and
training the random forest classifier using the image description features of the labelled training examples;
storing parameters of the trained random forest classifier.
9. The method of clause 8, further including training the random forest classifier using the image description features for one-vs-the-rest determination of the successful class vs the multiple failure classes.
10. A method of root cause analysis from a failed process cycle image, including:
accessing a basis of Eigen images with which to analyze a failed production image; and
creating image description features for the failed production image based on a linear combination of the Eigen images;
accessing a random forest classifier trained to distinguish images from process cycles belonging to one of multiple failure classes; and
applying the random forest classifier to the image description features for one-vs-the-rest determination among the multiple failed classes, including scoring each of the multiple failed classes vs the rest and using resulting scores to select among the multiple failed classes as a likely root cause of the failed process cycle.
11. The method of clause 2, further including:
accessing a second random forest classifier upon determination that the image description features do not belong to the successful class, wherein the second random forest classifier is trained to distinguish images from process cycles belonging to one of the multiple failure classes; and
applying the second random forest classifier to the image description features, including scoring each of the multiple failure classes vs the rest and using resulting scores to select among the multiple failure classes as a likely root cause of a failed process cycle.
12. A method of classifying genotyping process cycle images including:
determining and applying a threshold, from intensities of pixels in a grayscale production cycle image, with which to classify image pixels into bright and dark classes, transforming the grayscale image into a binary image;
segmenting the grayscale image and the transformed binary image into eight or more areas that separate systematic expected noise in the image from signal;
calculating average intensity values for the areas in the grayscale image and the transformed binary image;
accessing a random forest classifier trained to classify the images from process cycles, based on the average intensity values for the areas in the grayscale and the binary images, as belonging to a successful class or to a failure class and comparing a confidence score generated by the trained random forest classifier to a threshold and classifying the image as successful or failed.

13. The method of clause 12, further including:
applying a bilateral filter to preserve edges in the production cycle image before transforming the production cycle image.

14. The method of clause 12, further including:
applying Gaussian blur filter to remove speckle-like noise from the binary image after transforming the production cycle image.

15. The method of clause 12, further including:
applying morphology operations to fill holes in the binary image after transforming the production cycle image, wherein the morphology operations include erosion and dilation.

16. A non-transitory computer readable storage medium impressed with computer program instructions to train a random forest classifier for genotyping process cycle images, the instructions, when executed on a processor, implement a method comprising:
accessing labelled training examples for images from process cycles belonging to a successful class and multiple failure classes;
creating image description features for each labelled training example based on a linear combination of Eigen images;
training the random forest classifier using the image description features of the labelled training examples; and
storing parameters of the trained random forest classifier.

17. The non-transitory computer readable storage medium of clause 16, further implementing the method further comprising:
training the random forest classifier using the image description features for one-vs-the-rest determination of the successful class vs the multiple failure classes.

18. The non-transitory computer readable storage medium of clause 16, implementing the method further comprising:
accessing a basis of Eigen images;
ordering the basis of Eigen images according to a measure of variability explained;
selecting the top ordered basis of Eigen images that cumulatively explain variability above a threshold; and
analyzing the process cycle images using the selected basis of Eigen images.

19. The non-transitory computer readable storage medium of clause 16, wherein the random forest classifier includes 100 to 400 decision trees.

20. The non-transitory computer readable storage medium of clause 16, wherein the random forest classifier has a depth of 10 to 40.

21. The non-transitory computer readable storage medium of clause 18, implementing the method further comprising:
accessing a second random forest classifier upon determination that the image description features do not belong to the successful class, wherein the second random forest classifier is trained to distinguish images from process cycles belonging to one of the multiple failure classes; and
applying the second random forest classifier to the image description features, including scoring each of the multiple failure classes vs the rest and using resulting scores to select among the multiple failure classes as a likely root cause of the failed process cycle.

22. A non-transitory computer readable storage medium impressed with computer program instructions to classify genotyping process cycle images, the instructions, when executed on a processor, implement a method comprising:
determining and applying a threshold, from intensities of pixels in a grayscale production cycle image, with which to classify image pixels into bright and dark classes, transforming the grayscale image into a binary image;
segmenting the grayscale image and the transformed binary image into eight or more areas that separate systematic expected noise in the image from signal;
calculating average intensity values for the areas in the grayscale image and the transformed binary image;
accessing a random forest classifier trained to classify the images from process cycles, based on the average intensity values for the areas in the grayscale and the binary images, as belonging to a successful class or to a failure class and comparing a confidence score generated by the trained random forest classifier to a threshold and classifying the image as successful or failed.

23. The non-transitory computer readable storage medium of clause 22, implementing the method further comprising:
applying a bilateral filter to preserve edges in the production cycle image before transforming the production cycle image.

24. A system including one or more processors coupled to memory, the memory loaded with computer instructions to train a random forest classifier for process cycle images, when executed on the processors implement the instructions of clause 16.

25. The system of clause 24, further implementing actions comprising:
accessing a basis of Eigen images;
ordering the basis of Eigen images according to a measure of variability explained; and
selecting the top ordered basis of Eigen images that cumulatively explain variability above a threshold; and
analyzing the process cycle images using the selected basis of Eigen images.

26. The system of clause 24, wherein the random forest classifier includes 100 to 400 decision trees.

27. The system of clause 24, wherein the random forest classifier has a depth of 10 to 40.

28. The system of clause 25, further implementing actions comprising:
accessing a second random forest classifier upon determination that the image description features do not belong to the successful class, wherein the second random forest classifier is trained to distinguish images from process cycles belonging to one of the multiple failure classes; and
applying the second random forest classifier to the image description features, including scoring each of the multiple failure classes vs the rest and using resulting scores to select among the multiple failure classes as a likely root cause of the failed process cycle.

29. A system including one or more processors coupled to memory, the memory loaded with computer instructions to classify process cycle images, when executed on the processors implement the instructions of clause 22.

Computer System

Figure 11:
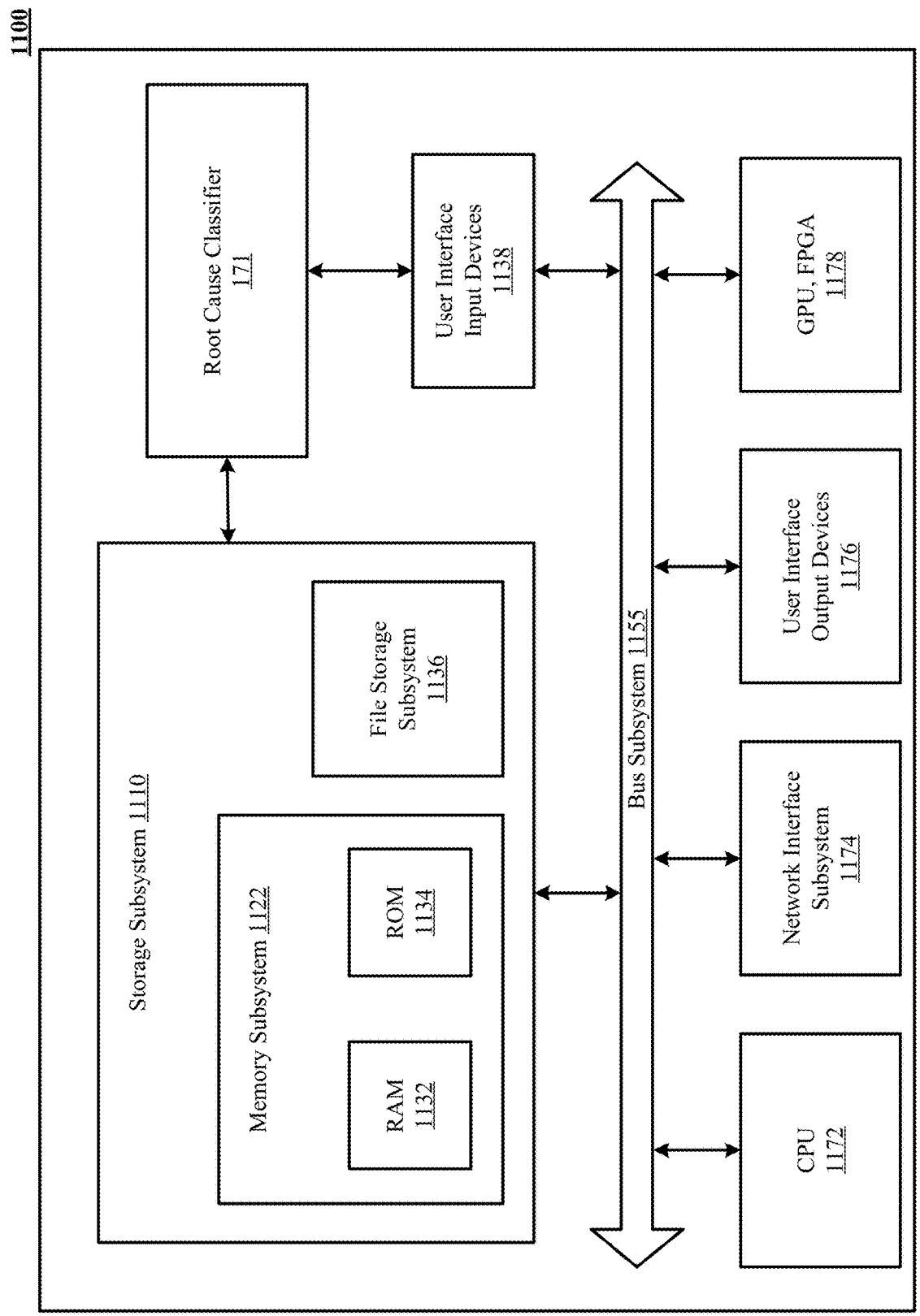
FIG. 11 is a simplified block diagram of a computer system that can be used to implement the technology disclosed.

FIG. 11 is a simplified block diagram of a computer system 1100 that can be used to implement the technology disclosed. Computer system typically includes at least one processor 1172 that communicates with a number of peripheral devices via bus subsystem 1155. These peripheral devices can include a storage subsystem 1110 including, for example, memory subsystem 1122 and a file storage subsystem 1136, user interface input devices 1138, user interface output devices 1176, and a network interface subsystem 1174. The input and output devices allow user interaction with computer system. Network interface subsystem provides an interface to outside networks, including an interface to corresponding interface devices in other computer systems.

In one implementation, the root cause classifier 171 to classify failed (or bad) images is communicably linked to the storage subsystem and user interface input devices.

User interface input devices 1138 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system.

User interface output devices 1176 can include a display subsystem, a printer, a fax machine, or non-visual displays such as audio output devices. The display subsystem can include a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system to the user or to another machine or computer system.

Storage subsystem 1110 stores programming and data constructs that provide the functionality of some or all of the modules and methods described herein. These software modules are generally executed by processor alone or in combination with other processors.

Memory used in the storage subsystem can include a number of memories including a main random access memory (RAM) 1132 for storage of instructions and data during program execution and a read only memory (ROM) 1134 in which fixed instructions are stored. The file storage subsystem 1136 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem in the storage subsystem, or in other machines accessible by the processor.

Bus subsystem 1155 provides a mechanism for letting the various components and subsystems of computer system communicate with each other as intended. Although bus subsystem is shown schematically as a single bus, alternative implementations of the bus subsystem can use multiple busses.

Computer system itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system depicted in FIG. 11 is intended only as a specific example for purposes of illustrating the technology disclosed. Many other configurations of computer system are possible having more or less components than the computer system depicted in FIG. 11.

The computer system 1100 includes GPUs or FPGAs 1178. It can also include machine learning processors hosted by machine learning cloud platforms such as Google Cloud Platform, Xilinx, and Cirrascale. Examples of deep learning processors include Google's Tensor Processing Unit (TPU), rackmount solutions like GX4 Rackmount Series, GX8 Rackmount Series, NVIDIA DGX-1, Microsoft' Stratix V FPGA, Graphcore's Intelligent Processor Unit (IPU), Qualcomm's Zeroth platform with Snapdragon processors, NVIDIA's Volta, NVIDIA's DRIVE PX, NVIDIA's JETSON TX1/TX2 MODULE, Intel's Nirvana, Movidius VPU, Fujitsu DPI, ARM's DynamicIQ, IBM TrueNorth, and others.

What is claimed is:

1. A method of training a random forest classifier for genotyping process cycle images, including:
   accessing labelled training examples for images from process cycles belonging to a successful class and multiple failure classes, each failure class corresponding to a different root cause of a failure;
   creating image description features for each labelled training example based on a linear combination of Eigen images;
   training the random forest classifier to identify specific features corresponding to the multiple failure classes using the image description features of the labelled training examples; and
   storing parameters of the trained random forest classifier.

2. The method of claim 1, further including:
   accessing a basis of Eigen images;
   ordering the basis of Eigen images according to a measure of variability explained; and
   selecting a top ordered basis of Eigen images that cumulatively explain variability above a threshold; and
   analyzing the process cycle images using the selected basis of Eigen images.

3. The method of claim 1, further including training the random forest classifier using the image description features for one-vs-the-rest determination of the successful class vs the multiple failure classes.

4. The method of claim 1, wherein the random forest classifier includes 100 to 400 decision trees.

5. The method of claim 1, wherein the random forest classifier has a depth of 10 to 40.

6. The method of claim 2, further including:
   accessing a second random forest classifier upon determination that the image description features do not belong to the successful class, wherein the second random forest classifier is trained to distinguish images from process cycles belonging to one of the multiple failure classes; and
   applying the second random forest classifier to the image description features, including scoring each of the multiple failure classes vs the rest and using resulting scores to select among the multiple failure classes as a likely root cause of a failed process cycle.

7. A non-transitory computer readable storage medium impressed with computer program instructions to train a random forest classifier for genotyping process cycle images, the instructions, when executed on a processor, cause the processor to:
   access labelled training examples for images from process cycles belonging to a successful class and multiple failure classes, each failure class corresponding to a different root cause of a failure;
   create image description features for each labelled training example based on a linear combination of Eigen images;
   train the random forest classifier to identify specific features corresponding to the multiple failure classes using the image description features of the labelled training examples; and
   store parameters of the trained random forest classifier.

8. The non-transitory computer readable storage medium of claim 7, wherein the instructions further cause the processor to:
   train the random forest classifier using the image description features for one-vs-the-rest determination of the successful class vs the multiple failure classes.

9. The non-transitory computer readable storage medium of claim 7, wherein the instructions are further configured to:
   access a basis of Eigen images;
   order the basis of Eigen images according to a measure of variability explained;
   select a top ordered basis of Eigen images that cumulatively explain variability above a threshold; and
   analyze the process cycle images using the selected basis of Eigen images.

10. The non-transitory computer readable storage medium of claim 7, wherein the random forest classifier includes 100 to 400 decision trees.

11. The non-transitory computer readable storage medium of claim 7, wherein the random forest classifier has a depth of 10 to 40.

12. The non-transitory computer readable storage medium of claim 9, wherein the instructions are further configured to cause the processor to:
   access a second random forest classifier upon determination that the image description features do not belong to the successful class, wherein the second random forest classifier is trained to distinguish images from process cycles belonging to one of the multiple failure classes; and
   apply the second random forest classifier to the image description features, including the processor being further configured to score each of the multiple failure classes vs the rest and use resulting scores to select among the multiple failure classes as a likely root cause of a failed process cycle.

13. A system including one or more processors coupled to memory, the memory loaded with computer instructions to train a random forest classifier for genotyping process cycle images, when executed on the one or more processors cause the one or more processors to:
   access labelled training examples for images from process cycles belonging to a successful class and multiple failure classes, each failure class corresponding to a different root cause of a failure;
   create image description features for each labelled training example based on a linear combination of Eigen images;
   train the random forest classifier to identify specific features corresponding to the multiple failure classes using the image description features of the labelled training examples; and
   store parameters of the trained random forest classifier.

14. The system of claim 13, wherein the instructions further cause the one or more processors to:
   access a basis of Eigen images;
   order the basis of Eigen images according to a measure of variability explained; and
   select a top ordered basis of Eigen images that cumulatively explain variability above a threshold; and
   analyze the process cycle images using the selected basis of Eigen images.

15. The system of claim 13, wherein the random forest classifier includes 100 to 400 decision trees.

16. The system of claim 13, wherein the random forest classifier has a depth of 10 to 40.

17. The system of claim 13, wherein the instructions further cause the one or more processors to:
   access a second random forest classifier upon determination that the image description features do not belong to the successful class, wherein the second random forest classifier is trained to distinguish images from process cycles belonging to one of the multiple failure classes; and
   apply the second random forest classifier to the image description features, including the one or more processors being configured to score each of the multiple failure classes vs the rest and use resulting scores to select among the multiple failure classes as a likely root cause of the failed process cycle.

* * * * *